(12) United States Patent
Augustine

(10) Patent No.: US 9,504,389 B2
(45) Date of Patent: *Nov. 29, 2016

(54) NON-INVASIVE CORE TEMPERATURE SENSOR

(71) Applicant: Augustine BioMedical & Design LLC, Eden Prairie, MN (US)

(72) Inventor: Scott D. Augustine, Deephaven, MN (US)

(73) Assignee: Augustine Biomedical and Design, LLC, Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,434

(22) Filed: Sep. 17, 2015

(65) Prior Publication Data

US 2016/0038036 A1 Feb. 11, 2016

Related U.S. Application Data

(63) Continuation of application No. 13/423,190, filed on Mar. 17, 2012, now Pat. No. 9,164,000.

(60) Provisional application No. 61/454,161, filed on Mar. 18, 2011.

(51) Int. Cl.
*A61B 5/01* (2006.01)
*A61B 5/00* (2006.01)
*A61B 17/12* (2006.01)
(Continued)

(52) U.S. Cl.
CPC ............. *A61B 5/01* (2013.01); *A61B 5/6833* (2013.01); *A61B 5/7246* (2013.01); *A61B 5/743* (2013.01); *A61B 17/12* (2013.01); *A61F 7/007* (2013.01); *G01K 1/165* (2013.01); *G01K 13/002* (2013.01); *A61B 2562/0276* (2013.01); *A61F 2007/0054* (2013.01); *A61F 2007/0071* (2013.01); *A61F 2007/0096* (2013.01)

(58) Field of Classification Search
CPC ........ G01K 1/16; G01K 13/002; A61B 5/01; A61B 5/6832
USPC .......................................... 600/549
See application file for complete search history.

(56) References Cited

U.S. PATENT DOCUMENTS 4,878,184 A * 10/1989 Okada ..................... G01K 7/42
374/107
5,791,907 A * 8/1998 Ramshaw ............ G09B 23/285
434/262
(Continued)

FOREIGN PATENT DOCUMENTS

EP            03399061         11/1990

OTHER PUBLICATIONS

International Preliminary Report on Patentability for International Application No. PCT/US2012/029565, Sep. 24, 2013, 11 pages.
(Continued)

*Primary Examiner* — Michael C Stout
(74) *Attorney, Agent, or Firm* — Fredrikson & Byron, P.A.

(57) ABSTRACT

A core temperature sensor and a method of using such a sensor to non-invasively measure a temperature of a core thermal compartment of a human body or other mammals. A heater of the core temperature sensor heats a peripheral area to a temperature greater than the core temperature. A skin temperature sensor of the core temperature sensor monitors a cooling of the peripheral area to determine the core temperature.

44 Claims, 16 Drawing Sheets

(51) Int. Cl.
*A61F 7/00* (2006.01)
*G01K 1/16* (2006.01)
*G01K 13/00* (2006.01)

(56) References Cited

U.S. PATENT DOCUMENTS

| | | | | |
|---|---|---|---|---|
| 6,038,464 | A * | 3/2000 | Axelgaard | A61B 5/04087 600/391 |
| 6,495,229 | B1 * | 12/2002 | Carte | A61F 13/023 428/137 |
| 6,851,850 | B1 * | 2/2005 | Lee | G01K 1/083 374/163 |
| 2004/0076215 | A1 * | 4/2004 | Baumbach | G01K 1/16 374/29 |
| 2008/0050709 | A1 * | 2/2008 | Aruffo | G09B 19/00 434/262 |
| 2008/0214951 | A1 * | 9/2008 | Fritz | A61B 5/01 600/549 |
| 2009/0030289 | A1 * | 1/2009 | Katayama | A61B 5/0008 600/301 |
| 2010/0042013 | A1 * | 2/2010 | Cuesta Frau | A61B 5/0008 600/549 |
| 2010/0121156 | A1 * | 5/2010 | Yoo | G06F 19/3418 600/300 |
| 2010/0268113 | A1 * | 10/2010 | Bieberich | A61B 5/01 600/549 |
| 2010/0268114 | A1 * | 10/2010 | Van Duren | A61B 5/01 600/549 |
| 2011/0054575 | A1 * | 3/2011 | Ginsburg | A61F 7/12 607/105 |
| 2011/0213559 | A1 * | 9/2011 | Pollack | A61B 5/0008 702/19 |
| 2011/0224573 | A1 * | 9/2011 | Bar-Tal | A61B 18/1492 600/549 |
| 2011/0249701 | A1 * | 10/2011 | Bieberich | G01K 1/165 374/163 |
| 2013/0003776 | A1 | 1/2013 | Bieberich et al. | |
| 2013/0010828 | A1 | 1/2013 | Bieberich et al. | |

OTHER PUBLICATIONS

Yamakage "Evaluation of a newly developed monitor of deep body temperature" Journal of Anesthesia, 2002.

* cited by examiner

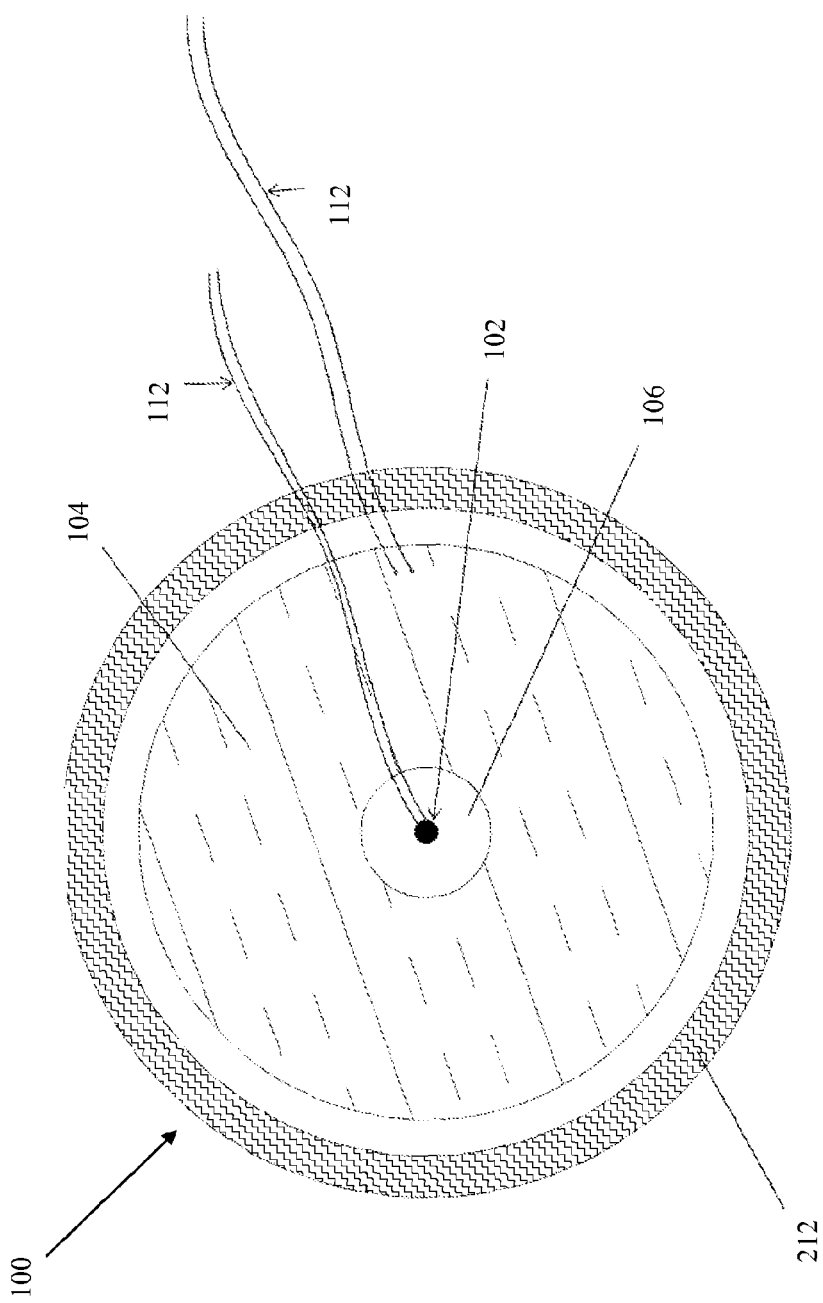

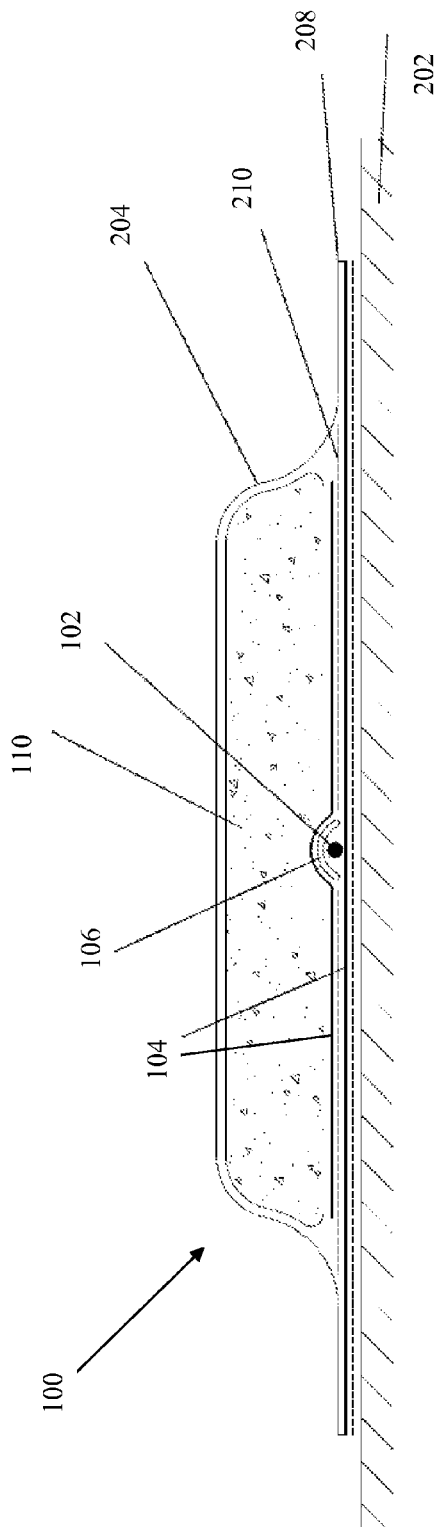
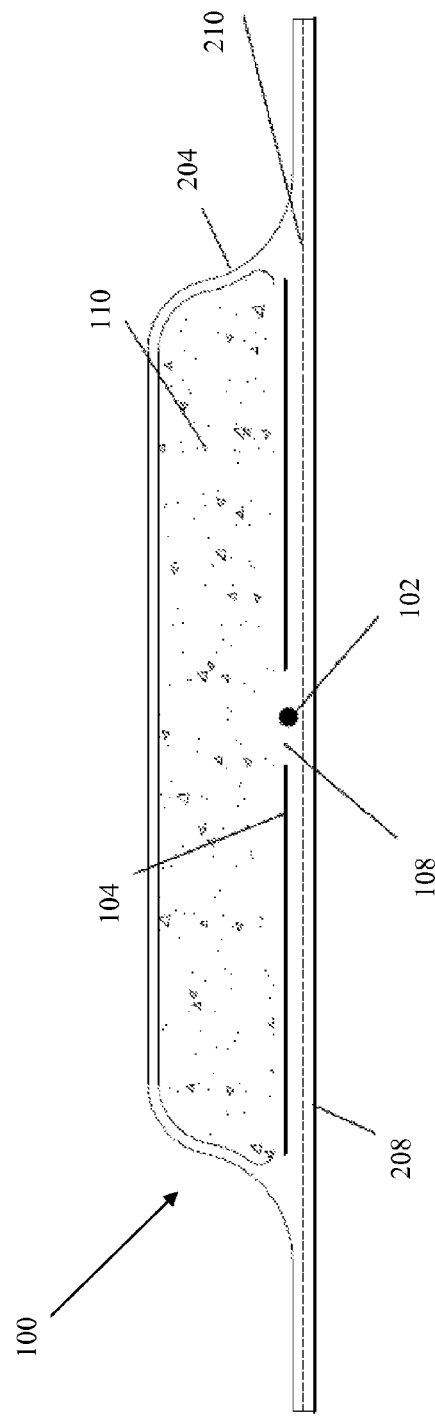
FIG. 3A
FIG. 3B

NON-INVASIVE CORE TEMPERATURE SENSOR

PRIORITY CLAIM

The present application is a continuation application of U.S. patent application Ser. No. 13/423,190, filed Mar. 17, 2012 and entitled "NON-INVASIVE CORE TEMPERATURE SENSOR", which claims priority to U.S. Provisional Patent App. No. 61/454,161, filed Mar. 18, 2011 and entitled "NON-INVASIVE CORE TEMPERATURE SENSOR," and which is hereby incorporated by reference.

TECHNICAL FIELD

The present invention relates to a temperature sensor for measuring the core temperature of a mammalian body. More specifically, the invention relates to a non-invasive temperature sensor for measuring the core temperature of a human body.

BACKGROUND

"Core" body temperature is the temperature of the vital organs of a person or animal. An abnormally elevated core body temperature occurs when an individual is in a febrile or hyperthermic state and can result in seizures, protein denaturation and even cell death. An abnormally low core body temperature causes an individual to be in a hypothermic state, which can affect and impair the rate at which chemical reactions in the body take place and possibly lead to respiratory or circulatory failure.

Accurate core body temperature measurements are clearly important for medical diagnosis in clinics, emergency rooms and operating rooms. Additionally, there are many occupations that can put the individual at risk for hypothermia or hyperthermia including: fire fighters, solders, athletes, military pilots and divers. There is a clear need for an accurate and non-invasive way to measure core body temperature.

The standard for "normal" core temperature of the human body is 37° C. or 98.7° F. However, research has shown that "normal" is actually a range of 37°+/−1° C. (96.8°-100.4° F.). Typically the body maintains its core temperature within a narrow range of 37°+/−0.5° C. In fact, vasomotor responses to changes in core body temperature can be detected with as little as a 0.1° C. deviation from baseline.

The temperature of the skin is generally recognized as being 3-10° C. cooler than the core body temperature. The actual gradient between skin and core temperatures depends on many factors including: the person's core temperature, ambient environmental temperature, wind and air movement, sweating or skin wetness for other reasons, the level of physical exertion, where on the body the skin is located, clothing, hydration and vasomotor tone.

The human body and all mammals have a "core" thermal compartment and a "peripheral" thermal compartment. The core compartment consists roughly of the central volume of the torso, head and neck. The core compartment includes all of the major organs. The operation of most physiologic functions is exquisitely sensitive to variations in temperature. Most physiologic functions are chemical reactions and chemical reactions are well known to be temperature dependent. Enzyme mediated or enzyme enhanced chemical reactions are even more temperature sensitive. Enzyme mediated chemical reactions slow dramatically with as little as a 1-2° C. drop in temperature. Therefore, protecting the core temperature and thus the temperature of the vital organs where chemical reactions sustain life, is paramount to survival.

The core compartment is surrounded by a thermally insulating layer of skin, subcutaneous tissue and fat, known collectively as the peripheral thermal compartment. Further, the entire volume of the arms and legs are in the peripheral thermal compartment. The purpose of the peripheral compartment is to thermally insulate the core compartment from environmental thermal stress, especially cold. By controlling the blood flow to the peripheral compartment, the temperature of the peripheral compartment is "allowed" to vary widely and sacrifice its heat in order to protect the temperature of the core compartment. For example, on a cold day with inadequate clothing, the skin and subcutaneous tissue surrounding the torso may be severely vasoconstricted, reducing the local blood flow and causing the peripheral compartment to be 5° C. or more cooler that the temperature of the core compartment directly beneath it. The peripheral compartment becomes a thermal insulator between the core compartment and the environment. The skin of the lower legs may be more that 10° C. colder than the core temperature on a cold day.

On a warm day, especially with exercise, the skin of the peripheral compartment may be equal to the temperature of the core compartment. In a hot environment, the tissues of the peripheral compartment are vasodilated causing an increase in skin blood flow in order to promote heat dissipation through the skin.

The temperature of the peripheral compartment is easy to assess with skin surface temperature measurements. However, as previously discussed, the temperature of the peripheral compartment varies widely and unpredictably relative to core temperature, depending on the ambient environmental temperature as well as many other external and internal factors. Therefore, the temperature of the skin and peripheral compartment is an unreliable indicator of core temperature.

At the present time, all true core temperature measurements are invasive. For example core temperatures can be directly measured in the: pulmonary artery, esophagus, rectum, bladder and tympanic membrane. Measuring the temperature in these locations is necessarily invasive and may be risky and therefore these locations are not suitable for routine temperature measurements.

A wide variety of other less invasive temperature monitoring sites have been tried. These include: oral, nasal, infrared (IR) tympanic membrane emissions, axillary and forehead skin. All of these sites have been shown to be influenced in an unpredictable way by peripheral compartment and ambient environmental temperatures. Therefore, these non-invasive measurements have proven to be inaccurate or unreliable indicators of core temperature.

A variety of thermometers have been developed that measure the skin temperature and the ambient environmental temperature and then use a mathematical calculation which is supposed to compensate for the affect of ambient environmental temperature on the peripheral compartment. For example, an existing device uses two thermistors that measure skin and ambient environmental temperature respectively. A microprocessor calculates a compensation factor for the effect of the ambient temperature on the skin. Another device comprises an infrared thermometer that estimates core body temperature by measuring the axillary or tympanic membrane temperature by IR emission. The device then calculates core body temperature using the arterial heat balance equation which is based on heat flow through a thermal resistance from the core to a location of temperature measurement such as the skin and then to the ambient environmental temperature. The core temperature is based on skin temperature with a compensation factor for the ambient environmental temperature. Neither of these techniques have proven to be reliable or accurate.

A proposed device comprises a thermometer with two temperature sensors and thermal insulation between the two sensors forming a heat flux transducer. A heat flux transducer measures heat flow. This device uses an additional layer of thermal insulation between the skin and the environment in order to allow the skin to eventually equilibrate to zero heat flux with the environment and supposedly is in simultaneous equilibrium with the core body temperature. It is doubtful that such a device can accurately and reliably measure core temperature but if it could, it would require a long time to reach thermal equilibrium between the various thermal compartments and the ambient environment.

Several devices use an overlaying heater that is carefully controlled to equal skin temperature, thus allowing the heat from the core to migrate to the skin surface but not be lost to the ambient environment. The overlaying heater adjusted to skin temperature is essentially a perfect insulator. One of these devices comprises a deep tissue thermometer that has two temperature sensors separated by a known thermal insulation layer forming a heat flux transducer. A heater overlays the temperature sensors and is controlled by the servo-controller to "null heat flux" meaning that the temperature of the heater is precisely maintained at skin temperature so that there is zero heat flow from the skin to the ambient environment. Since heat loss is prevented, the skin eventually equilibrates with the deeper core tissue as the core heat slowly migrates to the skin surface. Equilibration takes 15 minutes or more.

Other devices also comprise deep tissue thermometers with two sensors and an overlaying heater that is controlled to precisely equal skin temperature, thus preventing any heat loss to the ambient environment. Unlike devices which use a heat flux transducer to detect heat flow, these devices measure heater temperature directly and simply match it with the skin temperature resulting from heat migrating outward from the core thermal compartment.

All of these thermometers that include overlaying heaters operate the heater throughout the temperature measurement. Additionally, each of these devices carefully controls the temperature of the heater to match the skin temperature and thus the heater serves as a perfect thermal insulator between the skin and the ambient environment. However, since the heater is carefully controlled to equal skin temperature, the heater by definition, does not actively heat the skin. All of these thermometers require two temperature sensors, one for the skin and one for the heater. Finally, all of these thermometers require equilibration of the core temperature with the peripheral compartment and then eventually equilibration with the skin, which can take a relatively long time. The long equilibration time of 15 minutes or more makes these thermometers impractical for most core temperature measurement indications.

In summary, core body temperature can be measured directly but the measurement techniques are invasive, cumbersome or risky. Peripheral thermal compartment temperatures can be measured non-invasively and directly but are not accurate or reliable indicators of core body temperature. Peripheral temperature measured with heat flux transducers and overlaying heaters that are carefully controlled to equal the skin temperature, allow eventual thermal equilibrium between the core thermal compartment, peripheral thermal compartment and skin surface. These thermometers have been shown to have a good correlation with core body temperature but are very slow, expensive and complicated.

A reliable, non-invasive, accurate, inexpensive and fast (for example; less than 3 minutes) device for measuring core body temperature from the skin surface is needed.

SUMMARY

Certain embodiments of the invention focus on a core temperature sensor for non-invasively measuring a temperature of a core thermal compartment of a human body or other mammal. The core temperature sensor includes a skin temperature sensor, a heater, a relatively thick layer of thermal insulation, and a controller. The skin temperature sensor can be placed in conductive thermal contact with the skin over-laying a portion of the core thermal compartment. The heater has a relatively large surface area including a first surface facing the skin wherein a central region of the first surface of the heating element is positioned to surround the skin temperature sensor. The relatively thick layer of thermal insulation is proximate a second surface of the heater and opposite the first surface of the heater facing the skin. The controller can start and stop heat from the heater, and the controller is operable to analyze a skin temperature decay curve.

Certain embodiments of the invention include a core temperature sensor for non-invasively measuring a temperature of a core thermal compartment of a human body or other mammal. The core temperature sensor includes a skin temperature sensor, a heater, a relatively thick layer of thermal insulation, and an algorithm that may be run by a controller connected to the skin temperature sensor. The skin temperature sensor can be placed in conductive thermal contact with the skin over-laying a portion of the core thermal compartment. The heater may have a relatively large surface area comprising a first surface facing the skin and a central region of the first surface of the heating element is positioned to surround the skin temperature sensor. The heater may be capable of heating the skin proximate the skin temperature sensor to a minimum of 2 C greater than the temperature of the core thermal compartment and then is capable of rapidly discontinuing heating. The relatively thick layer of thermal insulation is proximate a second surface of the heater and opposite the first surface of the heater facing the skin. The controller is attached to the skin temperature sensor which is correlated with time to create a temperature-versus-time dissipation curve when the heating is discontinued by a controller. The algorithm may analyze the skin temperature dissipation curve to determine the intersection of the slopes of the rapid temperature decrease portion of the curve and of the slow temperature decrease portion of the curve.

BRIEF DESCRIPTION OF THE DRAWINGS

FIG. 2A is a core temperature sensor in accordance with an embodiment of the invention;

FIG. 3A is a cross sectional view of a core temperature sensor in accordance with an embodiment of the invention;

FIG. 3B is a cross sectional view of a core temperature sensor in accordance with an embodiment of the invention;

DETAILED DESCRIPTION

Figure 1:
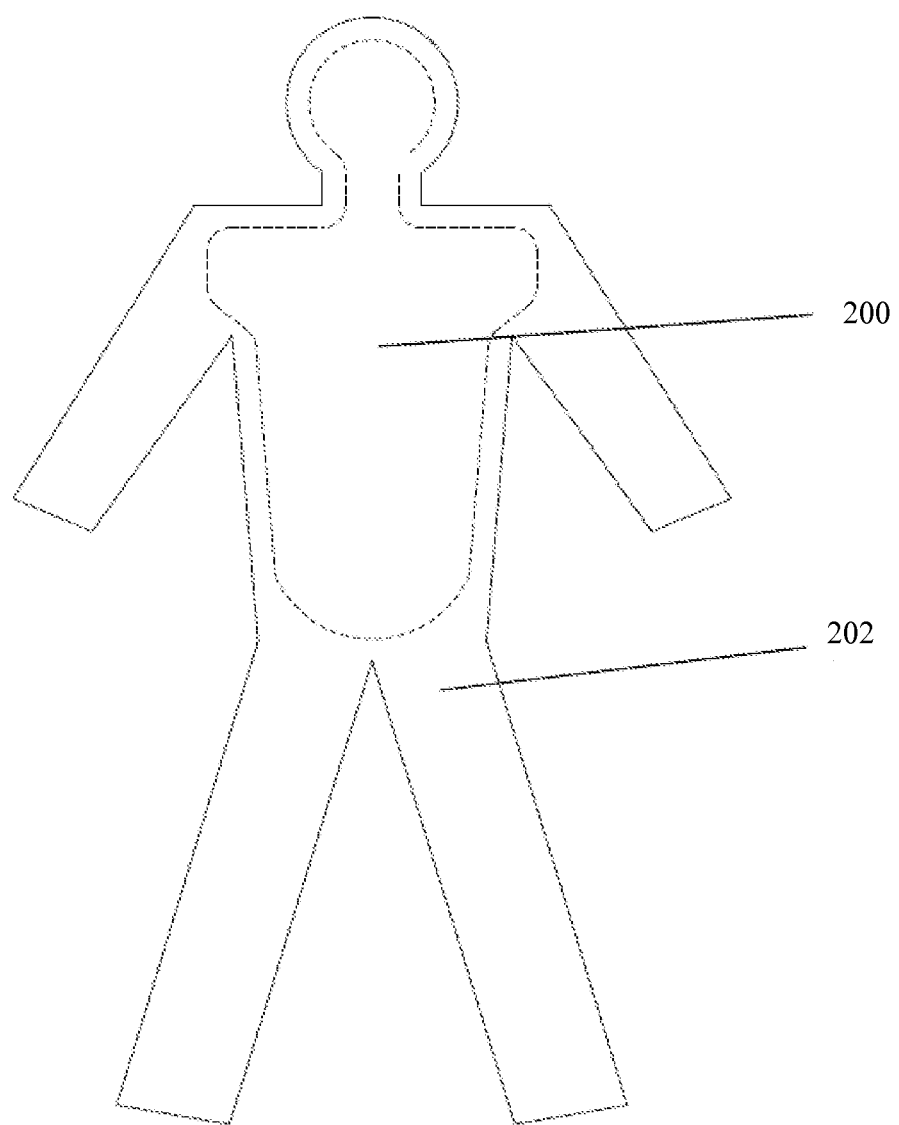
FIG. 1 is a schematic of a mammalian body comprising a core compartment surrounded by a peripheral compartment.

While multiple embodiments of the instant invention are disclosed, still other embodiments may become apparent to those skilled in the art. The following detailed description describes only illustrative embodiments of the invention. It should be clearly understood that there is no intent, implied or otherwise, to limit the invention in any form or manner to that described herein. As such, all alternative embodiments of the invention are considered as falling within the spirit, scope and intent of the disclosure.

This invention is fundamentally different than all other methods and devices for measuring core body temperature. All other devices known in the art attempt to measure the temperature of the core thermal compartment by measuring the temperature of the heat emanating outward from the core thermal compartment. The temperature of the core thermal compartment is either measured directly and invasively, or measured indirectly and non-invasively followed by various mathematical calculations, assumptions and compensation factors. The most accurate of the indirect, non-invasive measurements are made by creating a thermal equilibrium across the peripheral thermal compartment by preventing heat loss into the ambient environment with an overlaying heater that is carefully adjusted to skin temperature. In summary, all current non-invasive, skin surface measurement techniques of core body temperature, measure the heat emanating outward from the core thermal compartment to the skin where the temperature is measured.

In contrast, in an embodiment of the invention, excess heat is added through the skin to the peripheral compartment by a heater that is operating at a temperature that is higher than skin temperature. The overlaying heater adds heat to the skin and peripheral compartment until the temperature of the peripheral compartment is greater than core temperature or "overheated." When the temperature of the peripheral compartment reaches a temperature that is greater than core temperature, the heater is turned off. Thermal insulation is positioned between the heater and the ambient environment, which prevents the excess heat in the peripheral compartment from escaping into the ambient environment. Therefore, the excess heat in the peripheral compartment can only dissipate into the core thermal compartment, which it does until the two compartments are in thermal equilibrium at which time the flow of heat ceases.

A single temperature sensor on the skin surface can easily detect when the equilibrium between the core and peripheral compartments occurs. The excess heat in the peripheral compartment rapidly dissipates into the core thermal compartment until the temperatures of the core and peripheral compartments are equal and then the dissipation abruptly slows. The slope of the skin temperature-verses-time curve, i.e., the skin temperature dissipation curve (such as that shown in FIG. 8A), abruptly transitions from a steep slope of rapid temperature decrease (reflecting dissipation of the excess heat into the core thermal compartment), to an almost zero slope of very slow temperature decrease (when dissipation into the core thermal compartment ceases). The temperature of the underlying core thermal compartment correlates directly with skin temperature at the point of abrupt change in the slope of the temperature dissipation curve. We refer to this as the "thermal load dissipation" technique of measuring core body temperature.

Certain embodiments of the invention, such as the core temperature sensors 100 shown in FIGS. 2A, 2B, 3A, 3B, 3C, 4, 5, 6, 7A, and 7B, comprise a core temperature sensor 100 that attaches to the skin of the patient or person being monitored. Certain embodiments of the core temperature sensor 100 includes at least one skin temperature sensor 102 that is in conductive thermal contact with the patient's skin 103, wherein the skin temperature sensor 102 comprises a thermocouple, a thermistor or other electronic temperature sensor. Other types of thermometry such as thermographic inks could also be adapted to this technique.

Closely surrounding (but may be not physically touching), or overlaying the skin temperature sensor 102 and in conductive thermal contact with the patient's skin is the first surface of a heater 104. The heater 104 may be flexible, low thermal mass electric resistance heater 104. The surface area of the heater 104 should be of sufficient size to heat an adequate surface area of skin. In general, the larger the surface area heated, the more accurate the core temperature reading. However, the accuracy of the larger heater 104 must be balanced with the inconvenience of larger heaters. The heater 104, in certain embodiments of the invention, has a low thermal mass so that heat is not retained in the heater 104 when the electric power to the heater 104 is turned off. When the power is turned off, heat transfer to the skin from the heater 104 ceases very quickly. The heater 104 may be made from electrically conductive metal foil, electrically conductive fabric, electrically conductive film, electrically conductive ink, electrically conductive wire or any other suitable low thermal mass heater construction. The heater 104, in certain embodiments of the invention, is flexible so that it can conform to the contours of the body surface.

Alternately, the heater 104 could be made from many other higher thermal mass materials such as warm water pads, heated gels or even heated metals. The heater 104 could be made from materials that produce exothermic chemical reactions such as the oxidation of iron. In the case of higher thermal mass heaters or chemical heaters that cannot be turned off rapidly, the heater 104 may be physically separated from the skin to stop the heating when the heating period is finished. However the skin must remain thermally insulated from the ambient environment when the heater 104 is removed.

In an alternate embodiment, the heater 104 is not in conductive thermal contact with the skin. In one such embodiment, heat is transferred to the skin by radiant or convective means. If a radiant heater 104 is used, it may operate at a temperature that is significantly higher than the temperature at which a contact heater 104 may operate.

In certain embodiments of the invention, the skin temperature sensor 102 is located substantially in the central region on the first surface of the heater 104. In certain embodiments of the core temperature sensor 100, such as those shown in FIGS. 2A, 3A, 4, 5, 6, 7A, and 7B, the skin temperature sensor 102 may be separated from the first surface of the heater 104 by a thin layer of thermal insulation 106, minimizing the direct thermal impact of the heater 104 on the adjacent skin temperature sensor 102. Thus, when the first surface of the heater 104 is placed against the skin, the skin temperature sensor 102 is in conductive thermal contact with the skin and is at least partially thermally insulated from the heater 104. In certain embodiments of the invention, the layer of thermal insulation 106 between the skin temperature sensor 102 and the first surface of the heater 104 is sufficiently small so as to allow heat transfer to occur between the heater 104 and the skin adjacent the skin temperature sensor 102 without directly heating the skin temperature sensor 102.

Figure 2B:
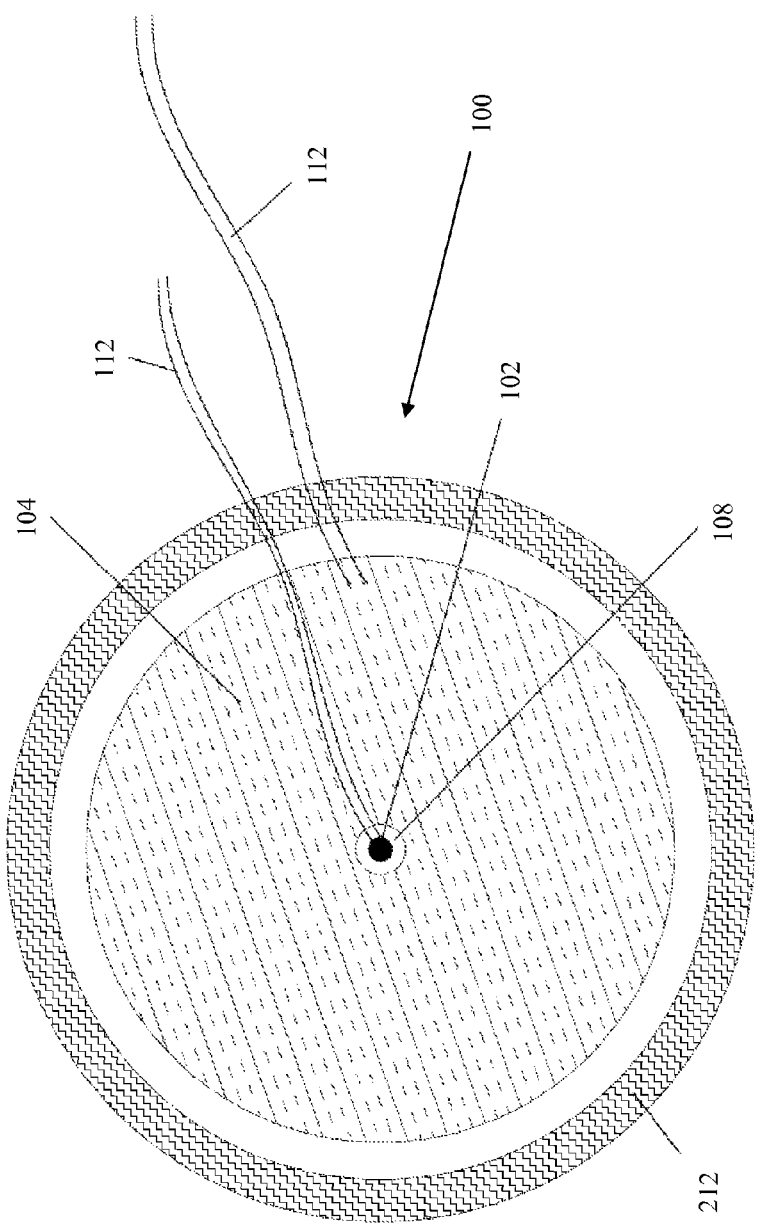
FIG. 2B is a core temperature sensor with an unheated zone located proximal the skin temperature sensor in accordance with an embodiment of the invention.
Figure 3C:
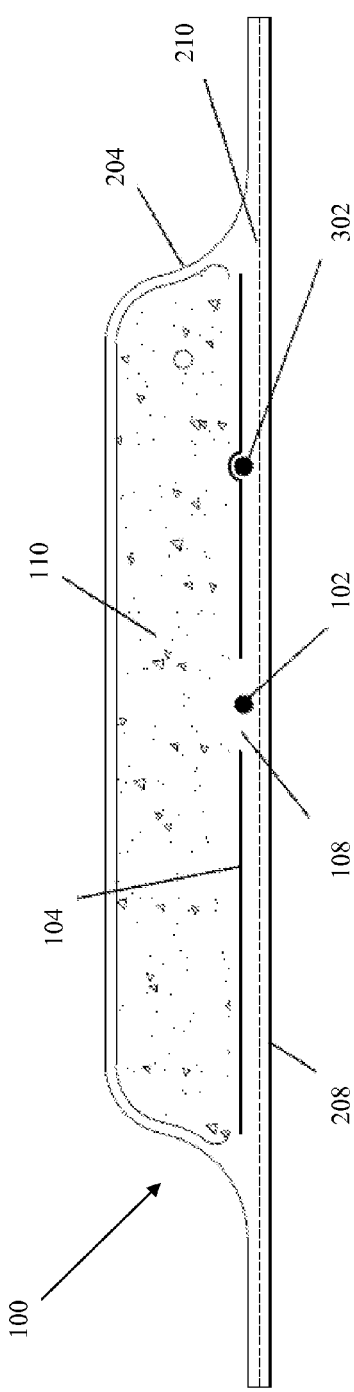
FIG. 3C is a cross sectional view of a core temperature sensor in accordance with an embodiment of the invention.

In certain embodiments of the core temperature sensor 100, such as that shown in FIGS. 2B, 3B, and 3C, the heater 104 has a hole 108 located substantially in the central region. The hole 108 is large enough diameter to accommodate the skin temperature sensor 102 without making a direct thermal contact with the sensor 102. In some embodiments, the hole 108 in the heater 104 is small enough to allow the skin proximate the skin temperature sensor 102 to be warmed without directly warming the skin temperature sensor 102. Since the heater 104 does not directly contact the skin temperature sensor 102, the output of this sensor 102 reflects skin temperature with minimal direct influence from the heater 104.

In certain embodiments of the invention, a relatively thick layer of thermal insulation 110 is located over the heater's 104 second surface, on the side away from the skin. This thick layer of thermal insulation 110 insulates the heater 104 and the measurement zone of skin under the heater 104, from the ambient environment. In certain embodiments of the invention, this thick layer of thermal insulation 110 is a high-loft non-woven fibrous material or closed-cell foam. However, other thermal insulations such as air spaces or open-celled foams are also anticipated. The specific material composition of the relatively thick layer of thermal insulation 110 is not important. Many thermally insulating materials could work. However, in certain embodiments, this layer 110 provides relatively sufficient thermal insulation of the warmed skin to limit heat loss to the ambient environment.

The type and the thickness of the thermal insulation 110 are chosen to provide a resistance to heat flow from the skin to the ambient environment that is greater than the resistance of heat flow from the skin into the body. In one dimension, the thermal resistance of a material can be defined as the thickness of the material divided by the thermal conductivity of the material. For skin of thickness 12.5 mm with a thermal conductivity of 0.37 Watts/(meter-° Kelvin), this equates to a thermal resistance of 0.0338° K/m In certain embodiments of the invention comprising a similar thickness of insulation 110 but with a thermal conductivity of 0.037 Watts/(meter-° Kelvin), the thermal resistance of the insulation 110 is ten times greater than that of the skin. It is possible to achieve comparable thermal resistances by varying the thickness and the thermal conductivity of the insulation 110 layer. In certain embodiments of the invention where a thin device is desirable, the insulation 110 layer would comprise a material with a higher thermal resistance. In some embodiments, a ratio of the thermal resistance of the insulation 110 layer to the skin resistance is greater than 1. In other embodiments this ration is between 2 and 5, and in yet other embodiments this ratio is greater than 5.

In certain embodiments of the invention, to improve the efficiency of the thermal insulation or to allow for a thinner thermal insulation layer 110, a second heater may be added as a "guard heater" (not shown). A second heater or guard heater may be approximately the same size surface area as heater 104 and is positioned on the upper side of the thermal insulation layer 110, the side opposite heater 104. Like heater 104, the guard heater may be made from electrically conductive metal foil, electrically conductive fabric, electrically conductive film, electrically conductive ink, electrically conductive wire or any other suitable low thermal mass heater construction. It is axiomatic that heat cannot radiate to an object that is equal or greater in temperature than the radiant source. The guard heater serves as the perfect thermal insulator between the skin temperature sensor 102 and the environment. To function as a guard heater, a guard heater temperature sensor is attached to the guard heater and the guard heater temperature is controlled to a specific temperature that does not allow radiant heat to escape to the environment, and yet assures that the guard heater does not add excess heat to the system. For example, the guard heater may be controlled to 37° C., which near the expected core temperature. Alternately, the guard heater may be controlled to the same temperature as the skin as measured by skin temperature sensor 102. The guard heater located on the upper surface of the thermal insulation layer 110, is prevented from influencing the measured skin temperature by the insulation layer 110 and yet absolutely assures that no heat is lost from the skin surface to the environment. Thus all excess heat in the peripheral compartment must flow into the core compartment and none is lost to the environment.

Figure 9:
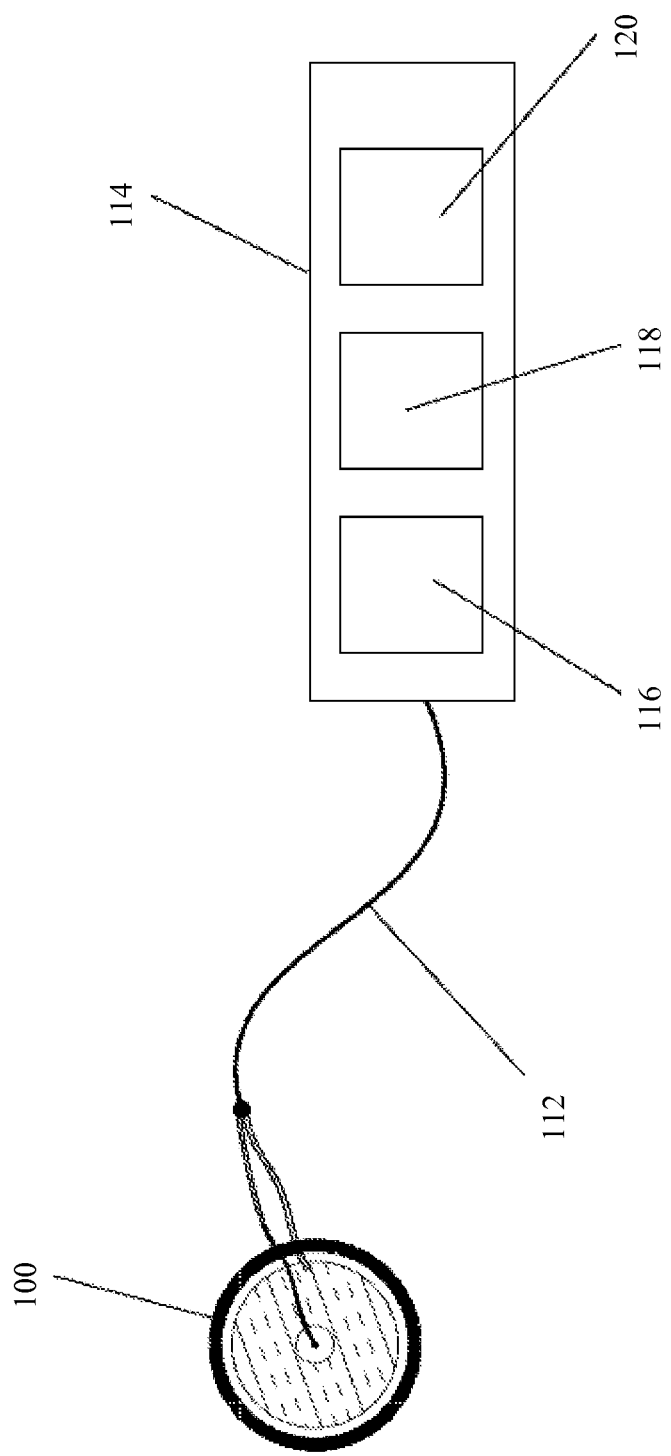
FIG. 9 is an illustration of a core temperature sensor in accordance with an embodiment of the invention.

In certain embodiments of the invention, such as that shown in FIG. 9, the heater 104 is operationally connected, for instance, via connector wiring 112 to a controller 114. In certain embodiments, the controller 114 includes a power source 116. In certain embodiments, the controller 114 includes a microprocessor 118. The controller 114 may be a simple "on-off" switch. In this case, the heat production of the heater 104 would be determined by the voltage of the current from the power source 116. When the desired skin temperature is achieved, the heater 104 is simply turned "off." Alternately, the controller 114 may be more sophisticated, regulating the heater 104 temperature to a specific temperature greater than skin temperature before turning "off" when the desired skin temperature is achieved. If a non-electric heater 104 is used, the heat can be turned "off" by physically separating the heater 104 from contact with the skin.

In certain embodiments of the invention, the skin temperature sensor 102 is operationally connected to a controller 114. The timing and/or temperature of the heater 104 is controlled using the skin temperature sensor 102 which is in thermal contact with the skin and at least partially thermally insulated from the surface of the heater 104. When the heater 104 is turned "off", the low thermal mass of the heater 104 causes it to rapidly cool and then the skin temperature sensor 102 only reflects skin temperature. The skin temperature dissipation curve is detected by the skin temperature sensor 102 and analyzed by a user or by the controller 114 as a mathematical algorithm or visual "algorithm," to determine core body temperature.

The simplest "algorithm", in accordance with certain embodiments of the invention, is for the user to watch a display of the sensed temperature on a display 120 of the controller 114. The user can watch the temperature decrease rapidly as the heat diffuses into the core thermal compartment 200 during the "thermal load dissipation" phase. When the user notes a sudden slowing of the temperature decline, equilibrium has been reached between the peripheral and core thermal compartments 202, 200 and the indicated temperature from the skin surface at that moment correlates with core body temperature. To create a thermal load dissipation curve, skin temperature is plotted against time. Therefore, a timing function is necessary and the output of the timing function is provided to the "algorithm."

Alternately, the skin temperature sensor 102 is connected to a microprocessor 118 in the controller 114, which determines the rapid change in the slope of the skin temperature dissipation curve during the "thermal load dissipation" phase. The microprocessor 118 measures skin temperature and time and can may be plot the relationship of these two variables automatically. When the plot of temperature versus time is complete and the core temperature is determined, the microprocessor 118 can be programmed to automatically display the new temperature and/or make an audible sound. In certain embodiments of this invention, the microprocessor 118 can also be programmed to automatically repeat the temperature measurement process at time intervals selected by the user, for example; every 15 minutes, and then automatically display the new temperature.

Some embodiments of the present invention provide a shutoff timer safety feature within controller 114 that cuts power to a heating element after a certain period of time has elapsed, irrespective of the feedback provided by a skin temperature sensor 102 concerning the skin temperature. That period of time is longer than it takes for the device to reach its operating temperature under normal conditions, but shorter than it takes to cause thermal burn injury.

The operation of the safety feature will now be described in accordance with certain embodiments. In operation, the controller 114 is first turned on and prompts the power source 116 to begin supplying power to the heater 104. The heater 104 continues to receive this power until the skin temperature sensor 102 senses a threshold temperature. The threshold temperature can be any desired temperature greater than core temperature. In some embodiments, the threshold temperature is 38° C., 40° C., 42° C., or other temperatures as discussed elsewhere herein. Once the skin temperature sensor 102 senses the threshold temperature, the controller 114 prompts the power source 116 to stop supplying power to the heater 104.

The shut-off timer operates simultaneously during the process just described. Regardless of the temperature sensed by the skin temperature sensor 102, the shut-off timer limits the amount of time that power is supplied to heater 104. This way, in case the skin temperature sensor 102 never reaches the threshold temperature, the shut-off timer only allows the power to be supplied for a limited time. This is an additional safety feature that helps to prevent patients from being exposed to temperatures at or above the threshold temperatures for a prolonged period of time.

Figure 10:
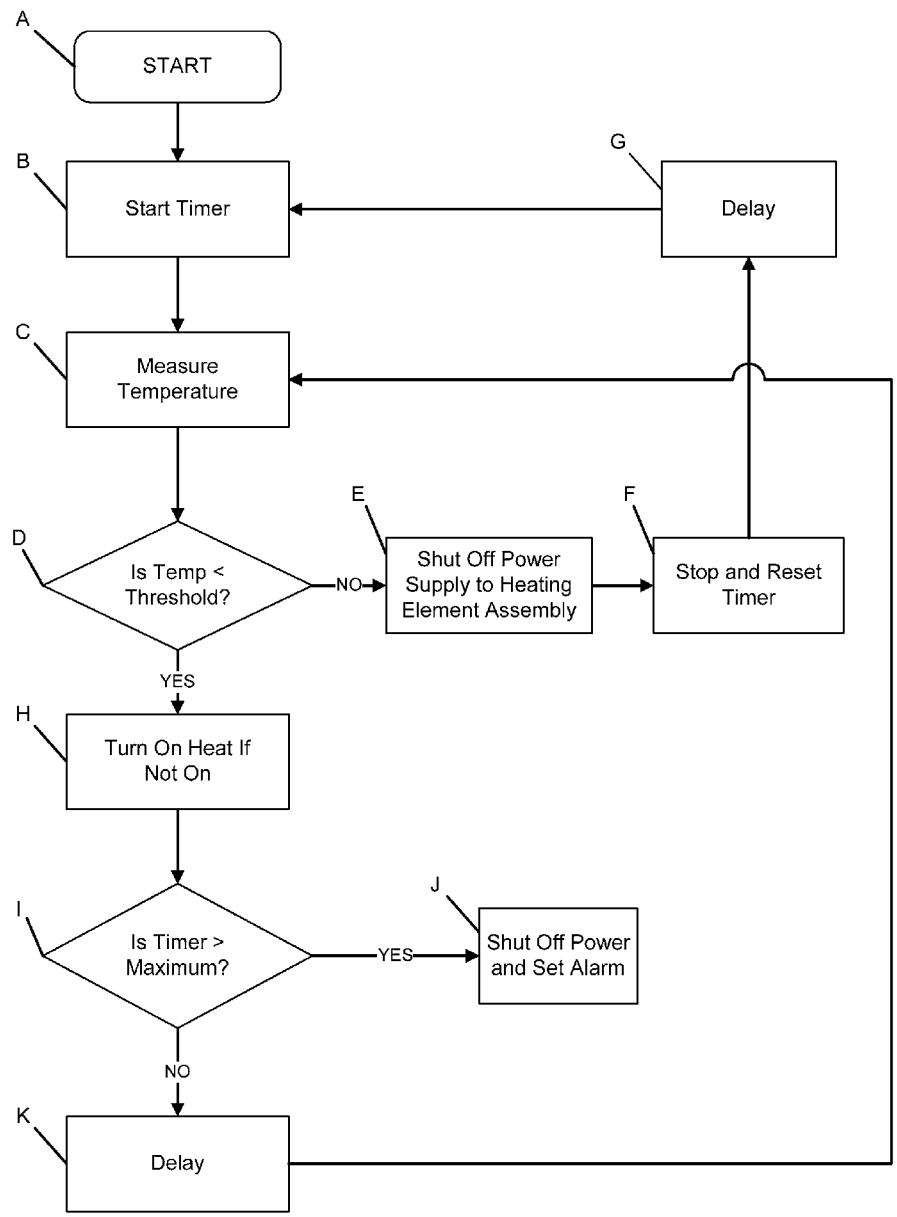
FIG. 10 is a flow diagram showing the operation of a core temperature sensor, according to some embodiments of the present invention.
Figure 11:
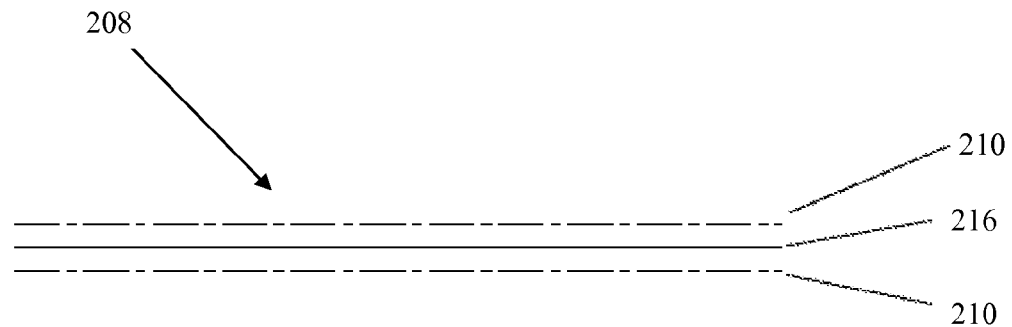
FIG. 11 is a cross sectional view of an adhesive layer, according to some embodiments of the present invention.
Figure 12:
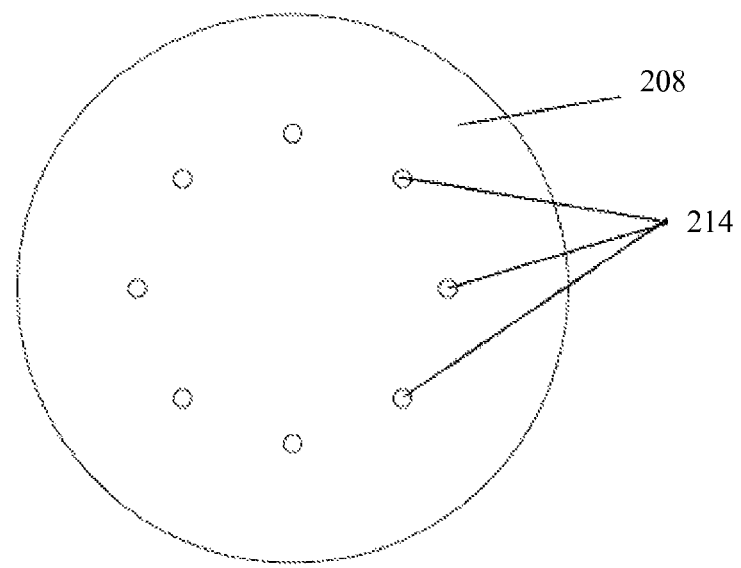
FIG. 12 is an illustration of an adhesive layer, according to some embodiments of the present invention.

The operation of the shut-off timer will now be described in conjunction with the method described more fully in FIG. 10. Once the controller 114 is turned on (step A), it prompts the shut-off timer to start (step B). The shut-off timer runs for a desired period of time and upon expiration of this period of time, if the heater 104 has not reached a threshold temperature (step D), the controller 114 prompts the power source 116 to stop supplying power to the heater 104 (step E). In addition, the controller 114 may sound an audio alarm and/or display a visible cue (step J). The expiration of the time period (step I) tells the medical personnel that the skin temperature sensor 102 may not be working or that the core temperature sensor may not be applied to the patient correctly.

Figure 4:
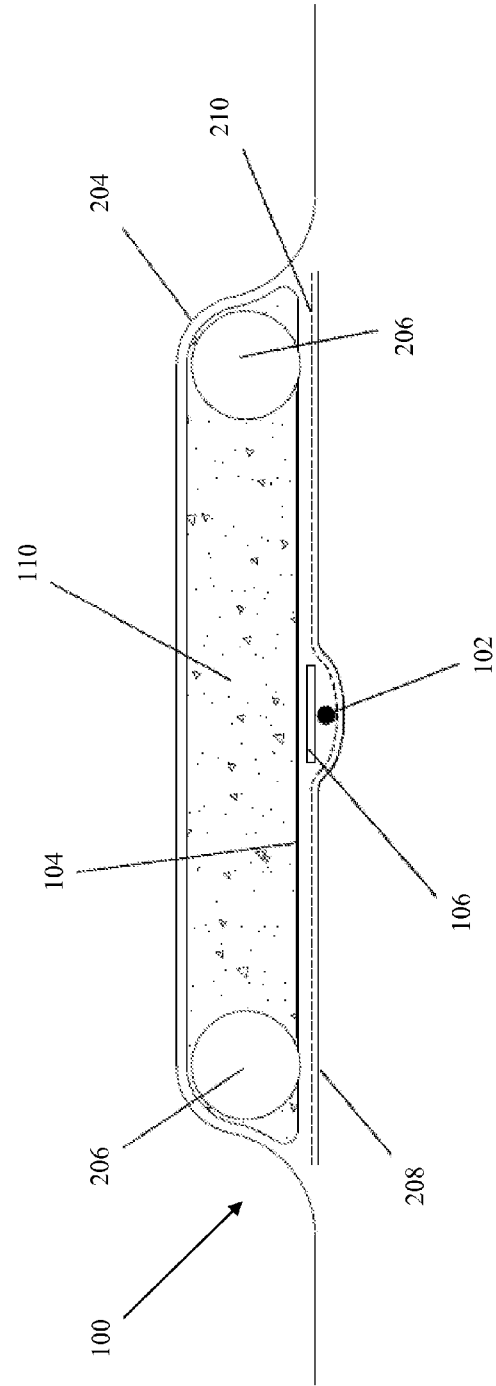
FIG. 4 is a cross sectional view of a core temperature sensor in accordance with another embodiment of the invention.
Figure 5:
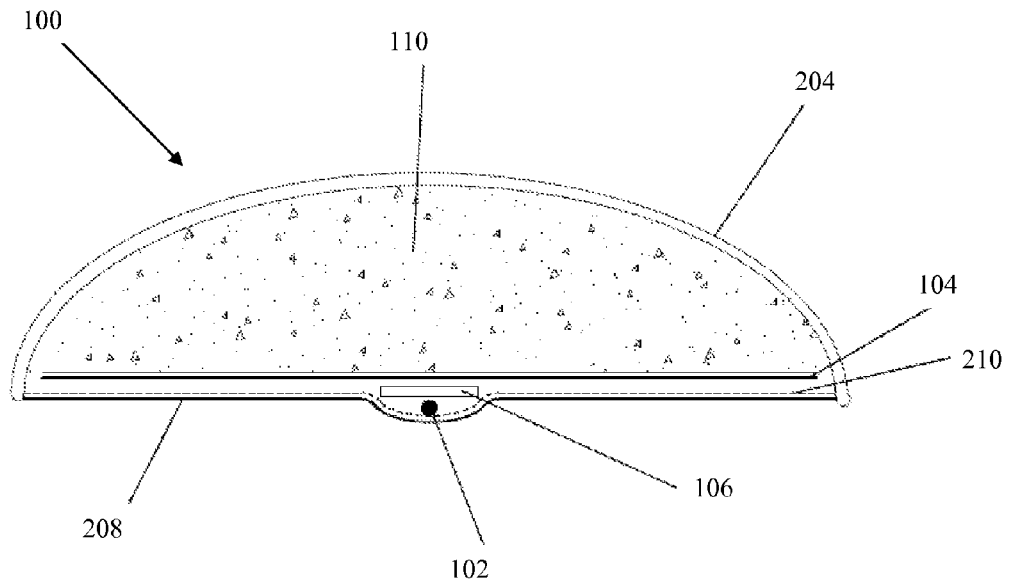
FIG. 5 is a cross sectional view of a core temperature sensor in accordance with an alternate embodiment of the invention.
Figure 6:
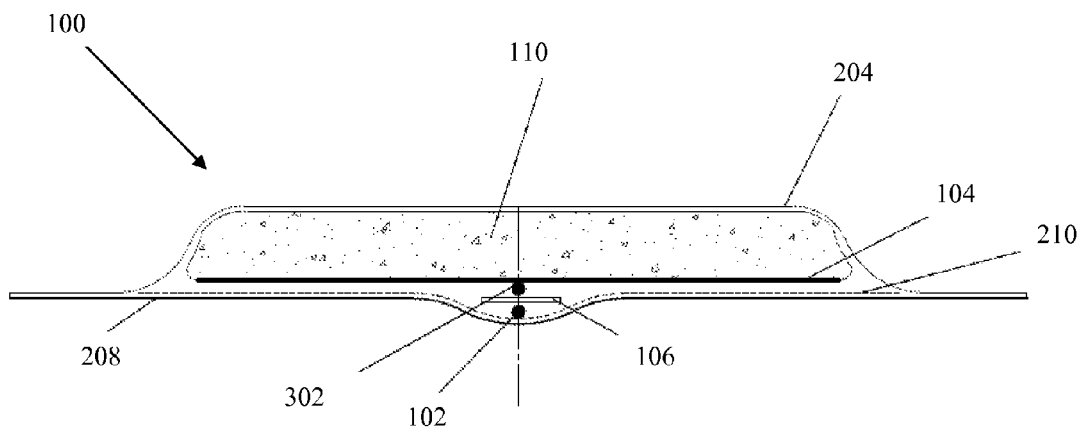
FIG. 6 is a cross sectional view of a core temperature sensor in accordance with yet another embodiment of the invention.

In certain embodiments of the invention, the skin temperature sensor 102 is enclosed in a hard or soft molded plastic, rubber or metal shell 205 (FIG. 4). Alternately, the skin temperature sensor 102 is enclosed in a soft plastic, waterproof pouch 204. In accordance with certain embodiments of the invention, the surface of the skin temperature sensor 102 that contacts the skin is a flexible, thin plastic film that allows conductive heat transfer between the skin and the skin temperature sensor 102 and heater 104. In another embodiment, the surface of the skin temperature sensor 102 that contacts the skin may be made of a rubber or silicon film, or a laminate that includes a metal foil layer.

Certain embodiments of the core temperature sensor 100 of the invention include a ring of material 206 that is near the perimeter of the heater 104. The ring of material 206 provides a ring of gentle pressure to the skin surrounding the skin temperature sensor 102. This pressure prevents blood from flowing laterally within the peripheral compartment 202 and diluting the temperature equilibrium between the peripheral and core thermal compartments 202, 200 with cool blood from the adjacent peripheral compartment 202. In certain embodiments of the invention, the ring of material 206 is similar to a flexible upside-down cup-like structure made of foam, plastic, rubber or other suitable materials.

In accordance with certain embodiments of the invention, the core temperature sensor 100 is attached to the skin of the patient using an adhesive layer 208. Adhesive 210 may be intermittently located on the adhesive layer 208 and the size of the adhesive layer 208 may be equal to or larger than the surface of the skin temperature sensor 102 that contacts the skin. As such, the adhesive layer 208 also serves as a contamination barrier between the sensor 102 and the patient. Alternately, it is anticipated that the core temperature sensor 100 can be attached by straps, tapes or any other attachment means, or held in place by the clinician or patient.

In certain embodiments, an adhesive layer 208 may be made of a thin plastic film with "double-faced" adhesive, so that one face adheres to the skin and the other face adheres to the core temperature sensor 100. This can be a single piece of film with adhesive applied to both sides. Alternately, embodiments of the invention include a skin temperature sensor 102 placed into a protective pouch (not shown) made of plastic film and sized to fit the skin temperature sensor 102. The protective pouch obviates the need to clean the skin temperature sensor 102 between patient uses. Some or all of the surface of the protective pouch 204 contacting the patient may include an adhesive layer 208.

In another embodiment, the protective pouch may be made of plastic film with an area of double-faced adhesive that approximates the size of the surface of the skin temperature sensor 102 that contacts the patient. One or more extensions of the plastic film can be provided to fold over and cover the skin temperature sensor 102. The side flaps may be create a substantially sealed pouch by adhesively attaching one or more of their outer edges to one another.

Whether the double-faced adhesive layer 208 is used alone or incorporated into a pouch, the adhesive faces may each be covered with removable liners to prevent inadvertent adhesion prior to use. In certain embodiments, the adhesive layer 208 is optimized by utilizing a different adhesive formulation on each face. For example, the adhesive on the face contacting the patient's skin is optimized for secure bonding to skin, yet must be detachable from the skin without damaging fragile skin. Since the heater 104 may cause localized sweating, certain moisture-tolerant adhesives including but not limited to hydrocolloids or hydrogels, are preferable on the face attached to the skin. Other adhesives are anticipated for the skin attachment face. Conversely, the adhesive on the face attached to the skin temperature sensor 102 may be formulated to securely bond to plastic film and yet be detachable without leaving a sticky adhesive residue or damaging the film layer of the core temperature sensor 100 when it is removed.

The accuracy of a temperature measurement can be dependent on the skin temperature sensor 102 being in conductive thermal contact with the skin. When the double-faced adhesive layer 208 is being attached to the skin temperature sensor 102 or to the skin, air could be trapped in a space between the two attachment surfaces and surrounded by an adhesive seal. This creates an air space that could be a significant thermal insulator, adversely affecting the accuracy of the core temperature sensor 100.

In certain embodiments, the double-faced adhesive layer 208 includes one or more air holes 214 punched or cut through the layer of film 216 and adhesives. The air holes 214 allow air that would otherwise be trapped, forming a bubble, or air space, between the adhesively bonded layers of film, to escape. The air holes 214 prevent the inadvertent formation of thermally insulating bubbles.

Figure 13:
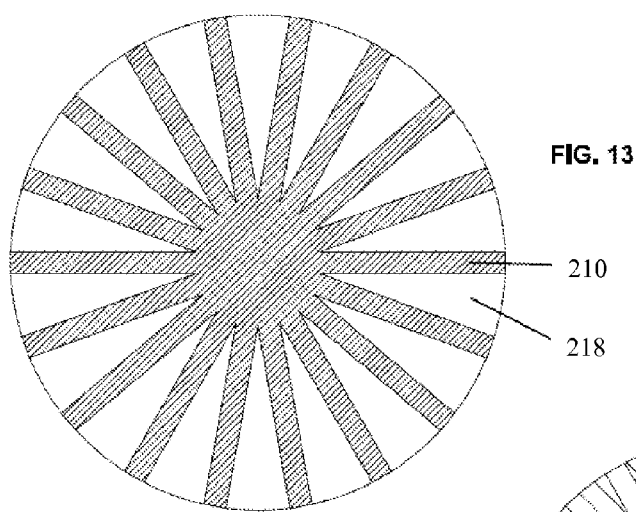
FIG. 13 is an illustration of an adhesive layer, according to some embodiments of the present invention.
Figure 14:
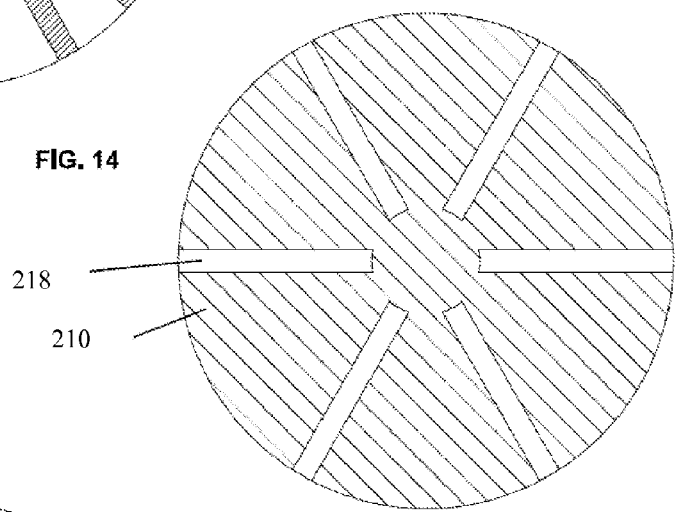
FIG. 14 is an illustration of an adhesive layer, according to some embodiments of the present invention.
Figure 15:
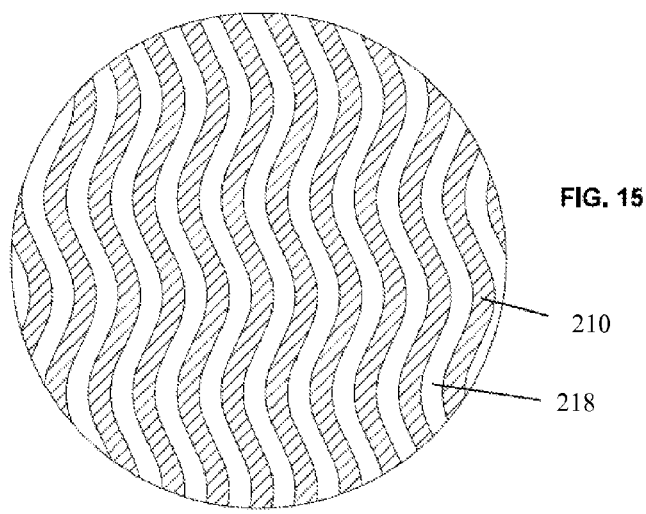
FIG. 15 is an illustration of an adhesive layer, according to some embodiments of the present invention.

In certain embodiments, the formation of thermally insulating bubbles between the adhesively bonded layers of film is prevented by applying the adhesive in a pattern that allows venting of the trapped air. For example, the adhesive 210 on one or both faces may be applied in a series of substantially parallel stripes (FIG. 15), or in a "star burst" pattern with radial stripes (FIG. 14), or in a dotted pattern. In all of these patterns and others that are anticipated, the air that could have been trapped, can escape through the non-adhesively bonded spaces 218 or air venting channels between the adhesive bonds. One advantage of a radial pattern (FIG. 13) is that a central adhesive dot can be formed by the merging radial lines proximate to the location of the skin temperature sensor 102 to provide optimal bonding at the skin temperature sensor 102 location.

The double-faced adhesive layer 208 may be applied to the skin temperature sensor 102 first to allow any trapped air to be vented through the air holes 214 or spaces between the adhesive bonds. Skin attachment can then be accomplished by a "rolling" motion, starting by contacting one edge 212 and then rolling toward the other, in order to minimize air trapping. A flexible embodiment of the core temperature sensor 100 may be flexed into an arcuate shape during attachment to aid in a 'rolling' application to minimize the risk of air being trapped between the skin temperature sensor 102 and the skin.

Figure 7A:
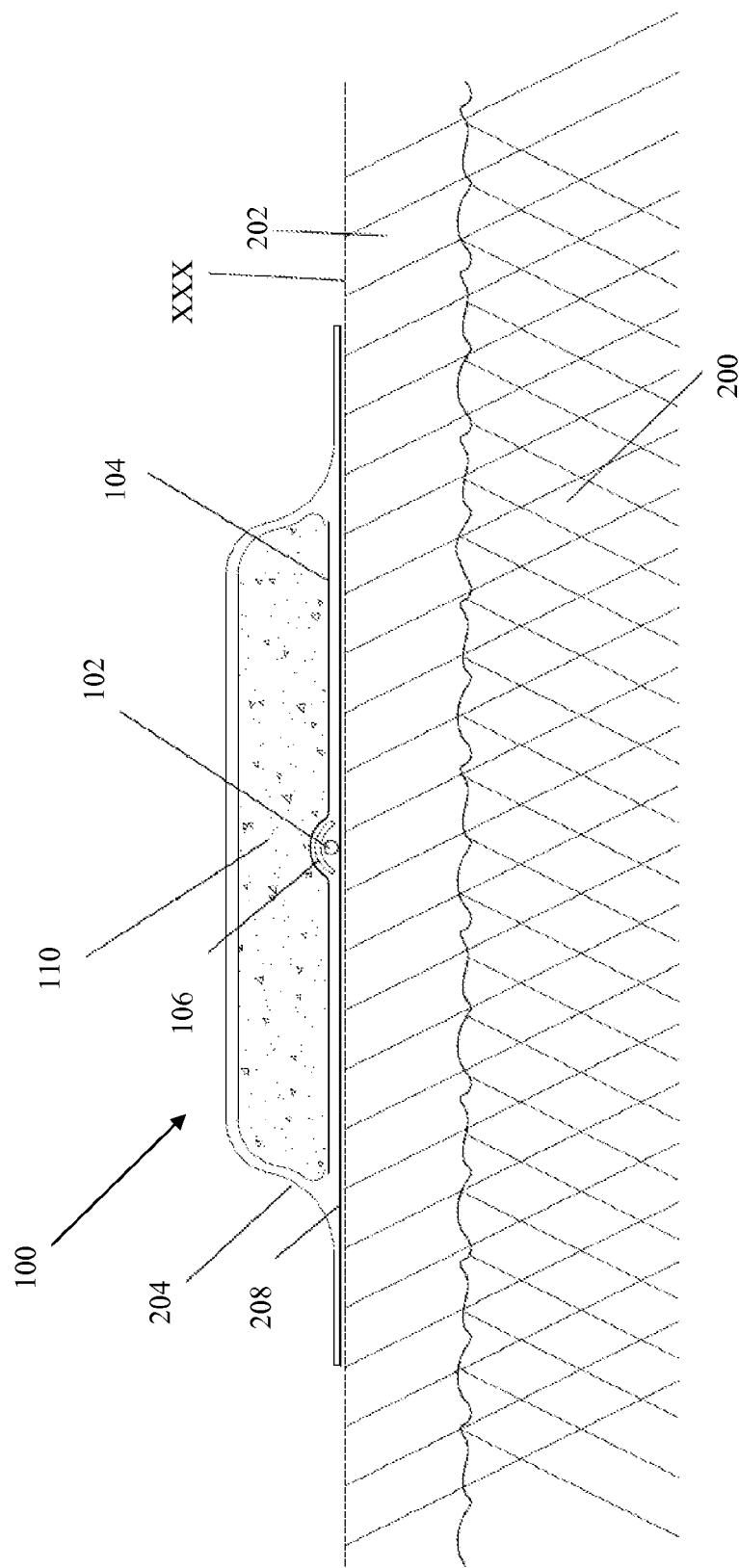
FIG. 7A is a cross sectional view of the core temperature sensor of FIG. 3 in use as initially positioning on the skin with the heater "off"
Figure 7B:
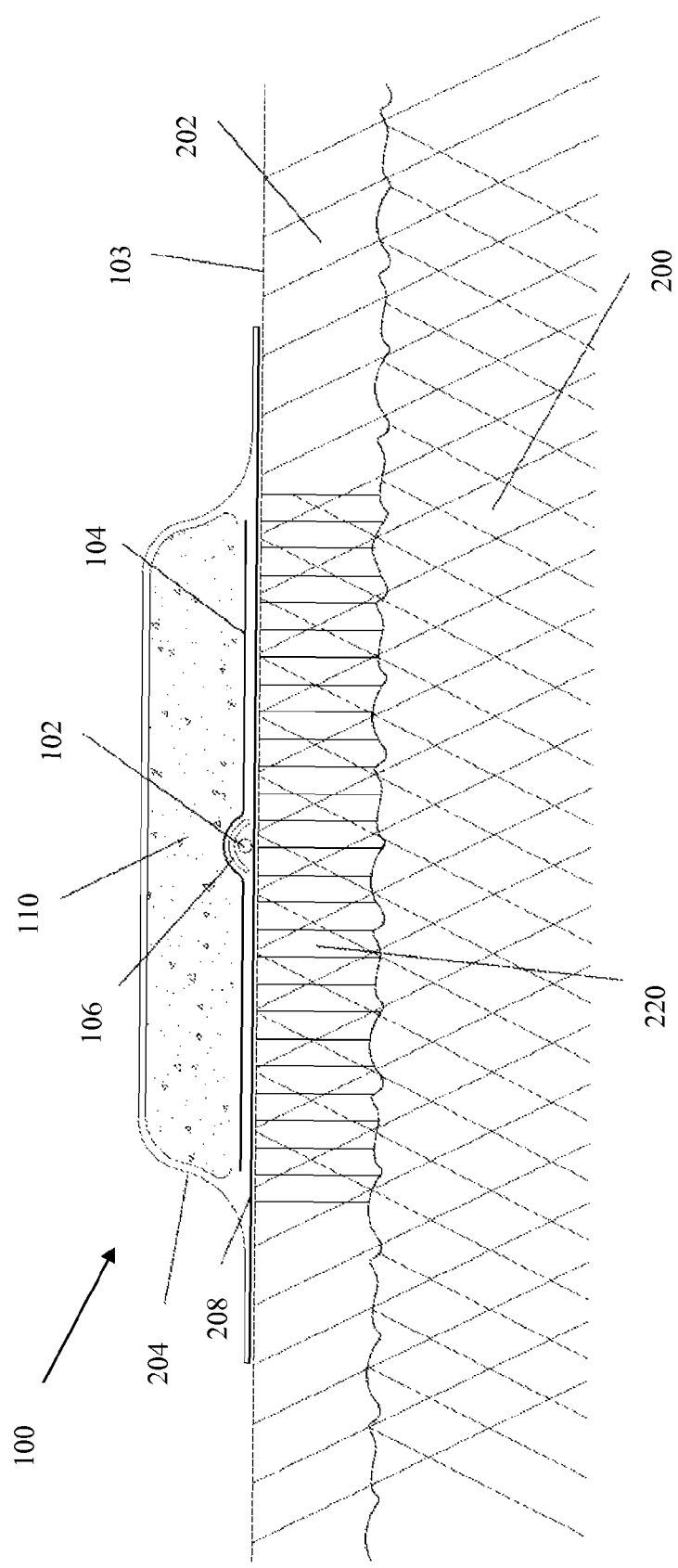
FIG. 7B is a cross sectional view of the core temperature sensor of FIG. 3 in use as positioning on the skin with the heater "on" illustrating an "over heated" peripheral compartment.

The method of using this non-invasive core temperature sensor 100, in accordance with certain embodiments of the invention, is fundamentally different than any other core temperature sensors. The core temperature sensor 100 of certain embodiments of the invention is attached to the skin over-laying the portion of the core thermal compartment 200 that is to be measured, as shown in FIG. 7A. In some embodiments of the invention, the core temperature sensor 100 is attached to the skin with a two-faced adhesive layer 208. The skin temperature sensor 102 is likely in conductive thermal contact with the skin and the over-laying heater 104 may be in conductive thermal contact with the skin. A thin, thermally conductive layer of plastic film 216 covers the lower surface of the skin temperature sensor 102 so that it is interposed between the skin and the skin temperature sensor 102 and the heater 104 but allows conductive heat transfer to occur.

In embodiments of the invention wherein the heater 104 is in conductive thermal contact with the skin, the heater 104 is energized to a temperature in the range of 2° C. to 40° C. greater than the core body temperature (39° C. to 77° C.). In embodiments of the invention wherein the heater 104 is not in conductive thermal contact with the skin, the temperature of the heater 104 may be significantly more than 40° C. higher than the core body temperature. The heater 104 warms the tissue of the peripheral compartment 202 to a temperature greater than the core body temperature, such as the overheated peripheral compartment 220 shown in FIG. 7B. The temperature of the skin and thus the temperature of the overheated peripheral compartment 220 are sensed by the skin temperature sensor 102 that is in conductive thermal contact with the skin. When the skin and tissue of the peripheral compartment 202 reaches a predetermined temperature that is greater than the predicted core body temperature, for example 40° C., the heater 104 is turned "off." This step may be repeated more than once to assure that the tissue in the peripheral compartment 202 below the heater 104 is heated to a temperature above core temperature or becomes overheated tissue 220. When the heater 104 is energized, the skin temperature sensor 102 primarily reflects the skin temperature and not heater 104 temperature, because the heater 104 may either have a hole 108 or a thin piece of thermal insulation 106 at the location of and over-laying the skin temperature sensor 102. Therefore, heat is not directly applied to the skin temperature sensor 102. If the heater 104 has a hole 108 to accommodate the skin temperature sensor 102, the edge of the heater 104 material may be close to the skin temperature sensor 102 but not in conductive thermal contact.

The actual core temperature determination may be made with the heater 104 "off." Due to the low thermal mass of the heater 104, the heater 104 loses its heat almost instantly when the electric power is turned off. Therefore, at that moment, the heater 104 adds no more heat to the skin and the non-energized heater 104 and over-laying, relatively thick thermal insulation 110 layer act together to prevent heat loss to the ambient environment.

The Laws of Thermodynamics dictate that the overheated tissue 220 in the peripheral compartment 202 will immediately begin to lose heat in all directions if possible. However, the heat is prevented from readily dissipating into the ambient environment by the relatively thick thermal insulation 110 layer over-laying the heater 104, which causes the core temperature sensor 100 to become a highly efficient thermal insulator. In certain embodiments of this invention, a second heater at the top surface of the thermal insulation layer 110 serves as a guard heater to further increase the efficiency of the thermal insulation of the temperature sensor 102 from the environment.

Since the heat is impeded from dissipating into the ambient environment, the excess heat is forced to dissipate into the adjacent core thermal compartment 200. The area of the peripheral compartment 202 that is chosen to measure the core temperature is often not an area of excessively thick subcutaneous fat. A thick layer of subcutaneous fat in the peripheral compartment 202 prolongs the time required to reach thermal equilibrium with the core thermal compartment 200. Therefore, areas such as the upper chest, side chest, neck, forehead or upper arm are generally chosen because these areas tend not to have excessively thick layers of subcutaneous fat. However, other body surface areas are also anticipated for core temperature measurement with this invention.

In certain embodiments, the core temperature sensor 100 is adapted to be placed in the axilla (arm pit) and may be held in this location with a strap around the upper arm or adhesively attached to the skin of the arm or chest. Alternately, the core temperature sensor 100 in the axilla can be squeezed between the upper arm and the chest, when the arm is at the patient's side. The skin temperature sensor 102 may be contacting the chest or the upper arm. While the upper arm does not strictly constitute "core body temperature," it can be a reasonable approximation due to the superficial location of the axillary artery on the inner arm.

Figure 7C:
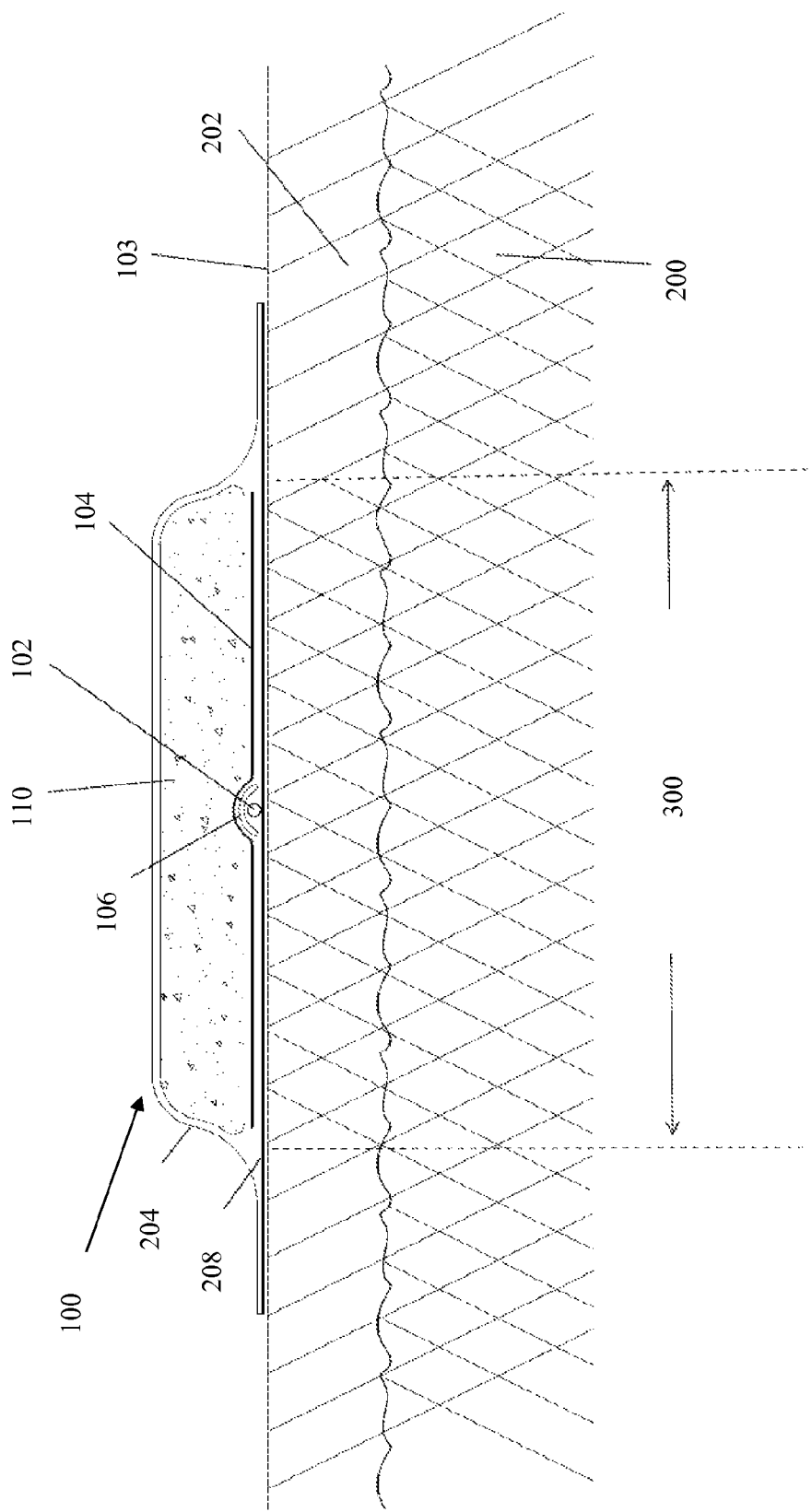
FIG. 7C is a cross sectional view of the core temperature sensor of FIG. 3 in use as positioning on the skin with the heater "off" illustrating equilibrated peripheral and core compartments.

The interface between the peripheral and core thermal compartments 202, 200 is a relatively large surface area and is close to the skin temperature sensor 102. Therefore, the dissipation of heat to the core thermal compartment or the "thermal load dissipation," occurs relatively quickly. The skin temperature sensor 102 will register a rapid drop in the temperature of the peripheral compartment 202. Then when the temperature of the peripheral and core thermal compartments 202, 200 approach equilibrium, shown as equilibrated core and peripheral compartments 300 in FIG. 7C, the precipitous fall in temperature suddenly slows. The algorithm for determining the core body temperature is based on the point of this change in the slope of the temperature dissipation curve.

Critical to understanding the difference between this invention and prior art core temperature thermometers that read skin temperature, is the fact that the algorithm for interpreting the input temperature data is fundamentally different from the prior art. In the prior art, heat from the core slowly diffuses outward into the peripheral compartment 202 and thus slowly raises the temperature of the peripheral compartment 202. With some of the prior art technologies, the temperature of the peripheral compartment 202 eventually equilibrates with the core temperature but it may take 20 minutes or more. The temperature-versus-time curve measured on the skin reflecting that equilibration starts well below core temperature. The temperature curve rises slowly at first and then rises even more slowly as it approaches equilibrium. A variety of complex mathematical calculations have been proposed for determining when equilibrium has been reached, because it is difficult to visually determine the point of equilibrium.

In certain embodiments of the invention, heat is added to the peripheral compartment 202 until it reaches a temperature that is greater than the core thermal compartment 200. Therefore, the starting point for the temperature-versus-time curve is typically higher than core temperature. When the heater 104 is turned off, the peripheral compartment 202 rapidly cools. Because the excess heat is dissipating into the highly-perfused core thermal compartment rather than warming the peripheral tissue, and because the blood vessels of the peripheral compartment 202 are dilated, thus maximizing local blood flow due to the heat, the temperature of the peripheral compartment 202 rapidly decreases, reflected by a relatively steep downward temperature-versus-time curve. When equilibrium has been reached between the peripheral and core thermal compartments 202, 200, the decreasing temperature curve abruptly slows and this slowing is reflected in the slope of the curve flattening. This point in the slope of the temperature decline curve is easily detectable, either with a visual inspection algorithm or a simple mathematical algorithm. The temperature at this point correlates with core temperature.

Some lateral heat dissipation to the adjacent cool peripheral compartment 202 tissues may occur. This lateral heat dissipation is primarily due to collateral blood flow, not simple thermal diffusion. The effect of this lateral dissipation on the temperature dissipation curve is minimized by creating a relatively large distance between the centrally located skin temperature sensor 102 and the lateral edge 212 of the heated area. However, the thermal equilibrium between the peripheral and core thermal compartments 202, 200 will be lost in time because of collateral blood flow between the heated and the surrounding un-heated peripheral compartment 202 tissues. This will cause the skin temperature to slowly decrease below core temperature.

Figure 8A:
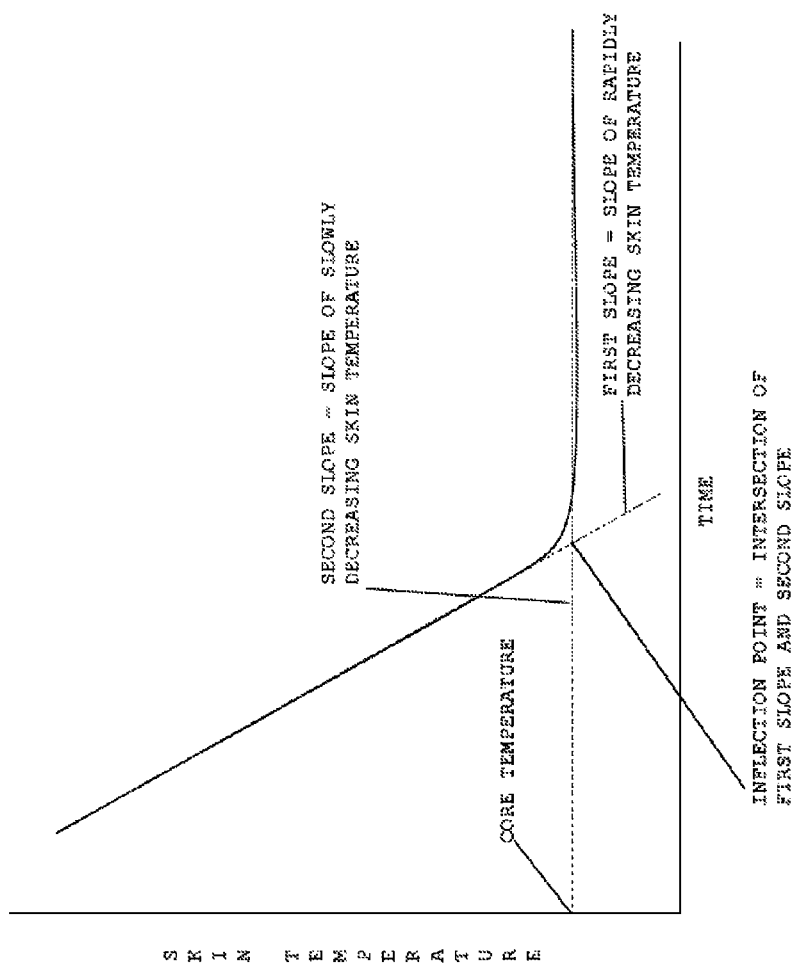
FIG. 8A is an illustration of a change in the skin temperature as a function of time in accordance with an embodiment of a method of the invention.
Figure 8B:
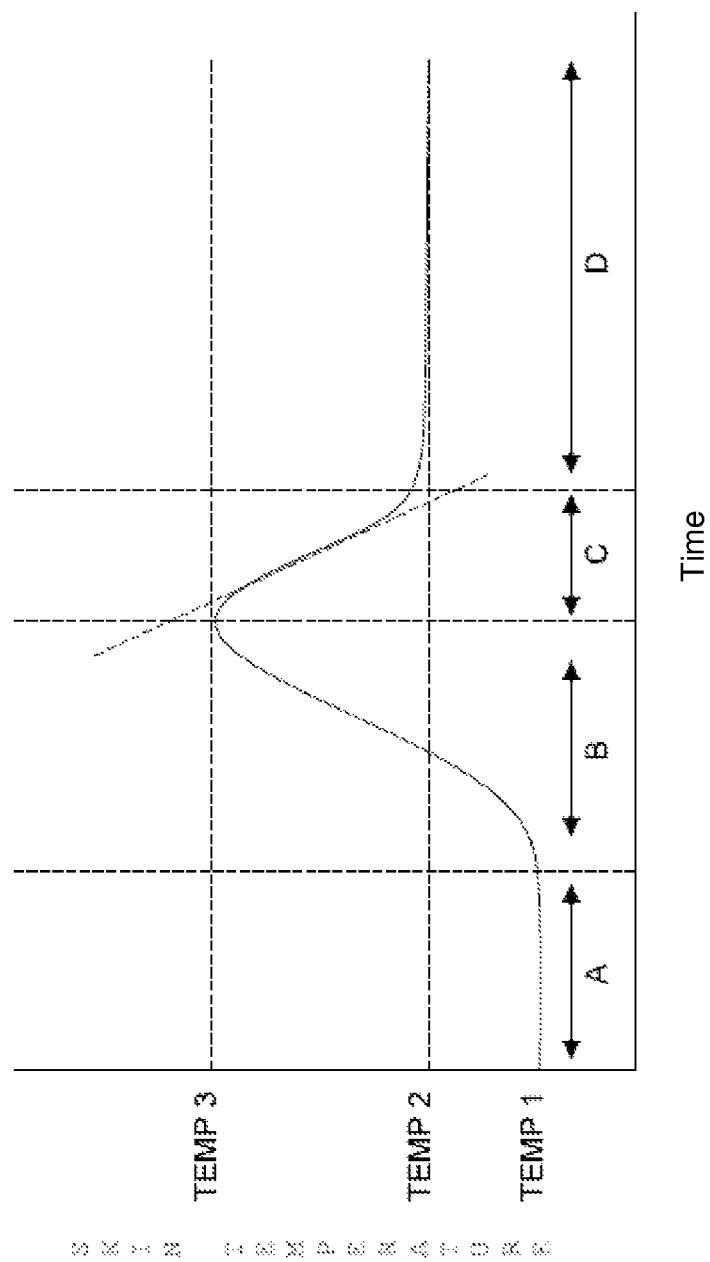
FIG. 8B is an illustration of a change in the skin temperature as a function of time in accordance with an embodiment of a method of the invention.

FIG. 8B is an illustration of a change in the skin temperature as a function of time in accordance with certain embodiments of a method of the invention. The following key explains the symbols used in FIG. 8B.

Time Spans:
A=Before Heating Is Initiated.
B=Heating Applied.
C=No Heating, Rapid Skin Temperature Decrease Thermal Dissipation Into Core.
D=No Heating, Slow Temperature Decrease, Peripheral compartment 202 Equilibrated With Core.

Skin Temperatures:
TEMP 1=Initial Skin Temperature.
TEMP 2=Skin Temperature After Peripheral compartment 202 Equilibration with Core.
TEMP 3=Maximum Skin Temperature Achieved or "Threshold" Temperature.

Figure 8C:
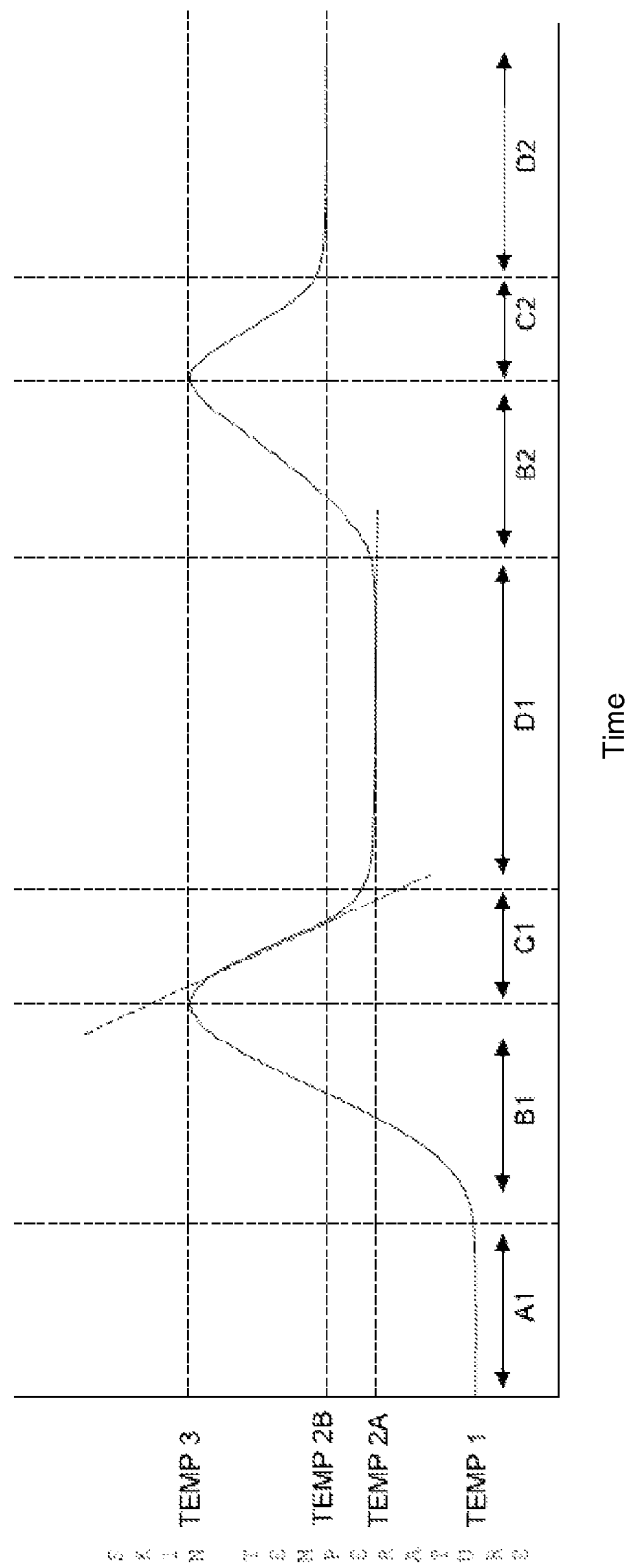
FIG. 8C is an illustration of a change in the skin temperature as a function of time in accordance with an embodiment of a method of the invention.

FIG. 8C is an illustration of a change in the skin temperature as a function of time in accordance with certain embodiments of a method of the invention. The following key explains the symbols used in FIG. 8C.

Time Span
A1=Before Heating Is Initiated.
B1=Heating Being Applied.
C1=No Heating, Rapid Skin Temperature Decrease Thermal Dissipation Into Core.
D1=No Heating, Slow Temperature Decrease, Peripheral compartment 202 Equilibrated With Core.
B2=Repeated Application of Active Heating.
C2=No Heating, Rapid Skin Temperature Decrease Thermal Dissipation Into Core.

D2=No Heating, Slow Temperature Decrease, Peripheral compartment 202 Equilibrated With Core.

Skin Temperature

TEMP 1=Initial Skin Temperature.

TEMP 2A=Skin Temperature After Peripheral compartment 202 Equilibration with Core at Initial Time.

TEMP 2B=Skin Temperature After Peripheral compartment 202 Equilibration with Core at a Second Time.

TEMP 3=Maximum Skin Temperature Achieved or "Threshold" Temperature.

The effect of this collateral flow of cool blood can be minimized by adding a ring of material 206 that surrounds the skin temperature sensor 102 and that can be mechanically pushed against the skin. Pressure is transmitted to the skin by the ring of material 206, occluding the blood vessels surrounding the skin temperature sensor 102 and minimizing the collateral blood flow from the surrounding peripheral compartment 202. The effect of adding this ring of material 206 is to stabilize the temperature curve in thermal equilibrium with the core thermal compartment for a longer time.

The heater 104 of certain embodiments also serves to accelerate the equilibration between the core and peripheral temperatures. The thermal diffusivity of human tissue (how fast the tissues can transfer heat) is significantly related to the flow of blood in the tissue. When a patient is cold and trying to conserve heat, their peripheral vessels constrict and slow the transfer of heat from the core thermal compartment to the peripheral compartment 202. When a patient is warm, the peripheral vessels dilate and speed the transfer of heat from the core thermal compartment to the peripheral compartment 202. In accordance with certain embodiments of the invention, the equilibration between the periphery and core thermal compartments is accelerated by locally raising the temperature and causing local vasodilation of the peripheral vessels. This is in contrast to existing "heat flux" sensors that are adjusted to equal skin temperature and prevent heat loss and, as such, do not vasodilate the peripheral vessels and thus require 20 minutes or more to reach equilibration between the peripheral and core thermal compartments 202, 200.

In accordance with an alternate embodiment of the invention, continuous temperature monitoring is provided by adding a second skin temperature sensor 302 (see FIG. 6) adjacent the first surface of the heater 104 and on the opposite side of the thin thermal insulation 106 adjacent the skin (or first) temperature sensor 102. Two temperature sensors 302, 102 separated by a thermal insulation 106 layer of known thermal conductivity constitutes a "heat flux transducer." The second temperature sensor 302 detects heater 104 temperature and, in certain embodiments of the invention, is used to control the heater 104 temperature to a "null heat flux." In this configuration the core temperature sensor 100 in accordance with certain embodiments of the invention operates as a continuous core temperature sensor comprising a heat flux transducer and an over-laying heater 104 controlled to a temperature that equals skin temperature. Rather than the 15-20 minutes of equilibration required by current null heat flow temperature monitors, the continuous core temperature sensor of certain embodiments of the invention equilibrates in a relatively short period of time due to the initially higher heater 104 temperatures. After the initial temperature is recorded using the thermal dissipation technique of this invention, the heater 104 in certain embodiments can be controlled to skin temperature to maintain thermal equilibrium so that continuous temperature measurements are possible. In this embodiment, the core temperature sensor 100 of this invention converts to a null heat flux type of monitor after the initial temperature determination. A second skin temperature sensor 302 may also be used in embodiments, such as that shown in FIG. 3C, having a hole 108 in the heater 104. In such embodiments, the second skin temperature sensor 302 measures heater 104 temperature and may be used to provide feedback to controller 114 regarding heater 104 temperature. Controller 114 may use the heater 104 temperature data in many ways, including helping ensure the heater 104 does not exceed a threshold temperature.

All other thermometers for measuring core temperature of the human body rely in some way on the migration of heat from the core thermal compartment 200 to a location that can be measured. The non-invasive core body temperature sensor 100 of certain embodiments of this invention is just the opposite. FIG. 8A is an illustration of a change in the skin temperature as a function of time in accordance with an embodiment of a method of the invention. In certain embodiments of the core temperature sensor 100 of the instant invention, heat is added to the peripheral compartment 202 until the temperature of the peripheral compartment 202 is greater than the core temperature or "overheated." At that point the heating is stopped and the rate of heat dissipation or "thermal load dissipation" is monitored at the skin surface. The core temperature is determined by the sudden change in the slope of the temperature dissipation curve (temperature versus time). The point where the steep slope of the "thermal load dissipation" phase and the sudden flattening of the slope in the thermal equilibrium between the peripheral and core thermal compartments 202, 200 phase intersect, correlates with the core body temperature.

Various modifications and additions may be made to the exemplary embodiments presented hereinabove without departing from the scope and intent of the present invention. For example, while the disclosed embodiments refer to particular features, the scope of the instant invention is considered to also include embodiments having different combinations of features different from and/or in addition to those described herein. Accordingly, the scope of the present invention is intended to embrace all such alternatives, modifications, and variations as falling within the scope and intent of the embodiments of the invention described herein.

The invention claimed is:

1. A core temperature sensor for non-invasively measuring a temperature of a core thermal compartment of a human body or other mammal comprising:
  a skin temperature sensor that is adapted to be placed in conductive thermal contact with the skin over-laying a portion of the core thermal compartment;
  a heater comprising a first surface adapted to face the skin, wherein a central region of the first surface of the heater is positioned to surround the skin temperature sensor;
  a layer of thermal insulation proximate a second surface of the heater and opposite the first surface of the heater facing the skin; and
  a controller to start and stop heat from the heater and to determine the core thermal compartment temperature, the controller configured to drive the heater to a predetermined temperature greater than the temperature of the core thermal compartment and then discontinue heating, permitting heat to rapidly diffuse into the core thermal compartment through thermal load dissipation, the controller operable to analyze a skin temperature-versus-time dissipation curve that occurs when the heat from the heater is stopped, wherein determination of the core thermal compartment temperature is established based on a slow temperature decrease portion of the curve determined by waiting for an empirically determined amount of time following the discontinuation of the heating, wherein the slow temperature decrease portion of the curve reflects a decreasing rate of change in the temperature measured by the skin temperature sensor and is indicative of reaching thermal equilibrium between the skin and the core thermal compartment.

2. A core temperature sensor for non-invasively measuring a temperature of a core thermal compartment of a human body or other mammal comprising:

a skin temperature sensor that is adapted to be placed in conductive thermal contact with the skin over-laying a portion of the core thermal compartment;

a heater comprising a first surface adapted to face the skin, wherein a central region of the first surface of the heater is positioned to surround the skin temperature sensor;

the heater is capable of heating the skin proximate the skin temperature sensor to a skin temperature greater than the temperature of the core thermal compartment and then is capable of rapidly discontinuing heating;

a layer of thermal insulation proximate a second surface of the heater and opposite the first surface of the heater facing the skin; and a controller attached to the skin temperature sensor which is correlated with time to create a skin temperature-versus-time dissipation curve when the heating is discontinued by the controller, the controller configured to drive the heater to a predetermined temperature greater than the temperature of the core thermal compartment and then rapidly discontinue heating, the controller operable analyze the skin temperature-versus-time dissipation curve to determine a slow temperature decrease portion of the curve, wherein the slow temperature decrease portion of the curve may be determined by waiting for an empirically determined amount of time following the rapid discontinuation of the heating to establish a temperature measurement of the core thermal compartment, wherein the slow temperature decrease portion of the curve reflects a decreasing rate of change in the temperature measured by the skin temperature sensor and is indicative of reaching thermal equilibrium between the skin and the core thermal compartment.

3. The core temperature sensor of claim 2, wherein the heater includes a hole in its central region and the skin temperature sensor is located within the hole.

4. The core temperature sensor of claim 2, wherein the central region of the first surface of the heater is positioned over the skin temperature sensor.

5. The core temperature sensor of claim 4, wherein the skin temperature sensor is separated from the first surface of the heater by a thin piece of thermal insulation.

6. The core temperature sensor of claim 2, wherein the heater is configured to be energized to a temperature equal to or greater than 39° C.

7. The core temperature sensor of claim 2, wherein the skin temperature sensor is one or more of a thermistor, a thermocouple, and a thermographic ink.

8. The core temperature sensor of claim 2, wherein the heater is one or more of an electrically conductive metal foil, an electrically conductive fabric, an electrically conductive film, an electrically conductive wire.

9. The core temperature sensor of claim 2, wherein the heater is one or more of a exothermic chemical reaction pad, a heated material including one or more of water, a gel, or a metal.

10. The core temperature sensor of claim 2, wherein the heater is flexible.

11. The core temperature sensor of claim 2, wherein the heater is adapted to be in conductive thermal contact with the skin over-laying the portion of the core thermal compartment, the heater operable to a temperature in the range of 2° C. to 40° C. greater than the temperature of the core thermal compartment.

12. The core temperature sensor of claim 2, wherein the layer of thermal insulation is one or more of a high loft non-woven fibrous material, a foam material, an air space.

13. The core temperature sensor of claim 2, wherein the controller is an on-off switch.

14. The core temperature sensor of claim 2, wherein the controller regulates the heater to achieve a prescribed temperature and/or time.

15. The core temperature sensor of claim 2, wherein the skin temperature sensor, the heater and the thermal insulation are enclosed in a water-proof plastic housing to form the core temperature sensor comprising the core temperature sensor, and the plastic housing includes a plastic film layer for separating the heater and skin temperature sensor from the skin.

16. The core temperature sensor of claim 15, wherein the first surface of the heater and skin temperature sensor are bonded to the plastic film layer of the plastic housing.

17. The core temperature sensor of claim 2, wherein the skin temperature sensor, the heater and the thermal insulation are enclosed in a water-proof plastic pouch to form the core temperature sensor and the plastic pouch includes a plastic film layer for separating the heater and core temperature sensor from the skin.

18. The core temperature sensor of claim 17, wherein the first surface of the heater and skin temperature sensor are bonded to the plastic film layer of the plastic pouch.

19. The core temperature sensor of claim 2, further comprising an adhesive layer.

20. The core temperature sensor of claim 19, wherein the adhesive layer is a double-faced adhesive comprised of a layer of film material with adhesive applied to both sides.

21. The core temperature sensor of claim 19, wherein the adhesive layer includes at least two different adhesive formulations, the formulation on one face is optimized for skin attachment and release and the formulation on the other face is optimized for attachment to and release from the core temperature sensor.

22. The core temperature sensor of claim 19, wherein the adhesive layer includes one or more holes cut through the film material and adhesive.

23. The core temperature sensor of claim 19, wherein the adhesive layer includes adhesive that has been applied in a stripe-like or dot pattern, wherein the space between the stripes or dots of adhesive constitutes one or more air venting channels.

24. The core temperature sensor of claim 2, further comprising a protective pouch attachment means.

25. The core temperature sensor of claim 19, wherein the adhesive layer comprises a protective pouch attachment means that includes a double-faced adhesive comprised of adhesive applied to both sides of one layer of the protective pouch.

26. The core temperature sensor of claim 19, wherein the adhesive layer includes one or more holes cut through a film material and the adhesive layer.

27. The core temperature sensor of claim 19, wherein the adhesive layer includes adhesive that has been applied in a stripe-like or dot pattern wherein the space between the stripes or dots of adhesive constitutes one or more air venting channels.

28. The core temperature sensor of claim 2, further comprising a raised ring of material near the perimeter which occludes collateral subcutaneous blood flow when pressure is applied by the core temperature sensor to the skin.

29. The core temperature sensor of claim 2, further comprising a second heater positioned on the opposite side of the thermal insulation layer from the skin heater.

30. The core temperature sensor of claim 29, further comprising a temperature sensor on the second heater and a controller wherein the controller adjusts the temperature of the second heater to approximate 37° C.

31. The core temperature sensor of claim 29, further comprising a temperature sensor on the second heater and a controller wherein the controller adjusts the temperature of the second heater to approximate the temperature of the skin as sensed by the skin temperature sensor.

32. The core temperature sensor of claim 2, wherein the controller is configured to analyze the skin temperature-versus-time dissipation curve to determine the intersection of the slopes of a rapid temperature decrease portion of the curve and of the slow temperature decrease portion of the curve.

33. The core temperature sensor of claim 2, wherein the heater is capable of heating the skin proximate the skin temperature sensor to a minimum of 2° C. greater than the temperature of the core thermal compartment and then is capable of rapidly discontinuing heating.

34. A method of non-invasively measuring a temperature of a core thermal compartment of a human body or other mammal, the method comprising:
  placing a skin temperature sensor in conductive thermal contact with a skin over-laying a portion of the core thermal compartment;
  placing a heater with a sufficiently large surface area such that a central region of a first surface of the heater is positioned to surround the skin temperature sensor and a layer of thermal insulation is proximate a second surface of the heater opposite the first surface of the heater facing the skin;
  energizing the heater to heat the skin to a predetermined temperature greater than the core thermal compartment temperature;
  de-energizing or removing the heater to stop heating the skin;
  monitoring with a controller, a cooling of the skin with the skin temperature sensor, and analyzing and interpreting one or more changes in the skin temperature-versus-time dissipation curve to determine the core thermal compartment temperature, wherein analyzing and interpreting one or more changes in the temperature-versus-time dissipation curve comprises waiting an empirically determined amount of time after stopping the heating of the skin to establish a temperature measurement for the core thermal compartment; and
  wherein analyzing and interpreting one or more changes in the temperature-versus-time dissipation curve comprises determining the slow temperature decrease portion of the curve established by a decreasing rate of change in the temperature measured by the skin temperature sensor and is indicative of reaching thermal equilibrium between the skin and the core thermal compartment.

35. The method of claim 34, further comprising energizing the heater to a temperature equal to or greater than 39° C.

36. The method of claim 34, further comprising de-energizing the heater when the skin is at a temperature greater than 39° C.

37. The method of claim 34, further comprising the controller providing instructions to enable a user of the core temperature sensor to interpret one or more changes in the skin temperature recorded by the skin temperature sensor during the steps of energizing and de-energizing the heater to determine the core thermal compartment temperature.

38. The method of claim 34, further comprising the controller analyzing one or more changes in the skin temperature recorded by the skin temperature sensor during the steps of energizing and de-energizing the heater to determine the core thermal compartment temperature, and indicating the core thermal temperature on the display.

39. The method of claim 34, further comprising the controller determining the temperature of the core thermal compartment based on an intersection point between a first slope of rapid dissipation in the skin temperature and a second slope of slow dissipation in the skin temperature.

40. A core temperature sensor for non-invasively measuring a temperature of a core thermal compartment of a human body or other mammal comprising:
  a skin temperature sensor that is adapted to be placed in conductive thermal contact with the skin over-laying a portion of the core thermal compartment;
  a heater comprising a first surface adapted to face the skin, wherein a central region of the first surface of the heater is positioned to surround the skin temperature sensor;
  the heater is capable of heating the skin proximate the skin temperature sensor to a skin temperature greater than the temperature of the core thermal compartment and then is capable of rapidly discontinuing heating;
  a layer of thermal insulation proximate a second surface of the heater and opposite the first surface of the heater facing the skin; a controller attached to the skin temperature sensor which is correlated with time to create a skin temperature-versus-time dissipation curve when the heating is discontinued by the controller, the controller configured to drive the heater to a predetermined temperature greater than the temperature of the core thermal compartment and then to discontinue heating; and the controller configured to analyze the skin temperature-versus-time dissipation curve, and to determine the slow temperature decrease portion of the curve, wherein the slow temperature decrease portion of the curve represents a decreasing rate of change in the temperature measured by the skin temperature sensor and is indicative of reaching thermal equilibrium between the skin and the core thermal compartment, wherein the slow temperature decrease portion of the curve may be determined by waiting for an empirically determined amount of time following the rapid discontinuation of the heating to establish a temperature measurement for the core thermal compartment.

41. A core temperature sensing system for non-invasively measuring a temperature of a core thermal compartment of a human body or other mammal, the system comprising:
  a heater adapted to be placed in thermal contact with the skin overlaying a portion of the core thermal compartment, the heater configured to heat the skin above the temperature of the core thermal compartment;
  a skin temperature sensor adjacent the heater, the temperature sensor adapted to be placed in thermal contact with the skin overlaying a portion of the core thermal compartment and to generate temperature data;

a display; and a controller operably coupled to the heater, the skin temperature sensor and the display, the controller configured to raise the temperature of the heater to a predetermined temperature above the temperature of the core thermal compartment, and to discontinue heating the skin when a threshold skin temperature is reached, the controller further configured to determine the temperature of the core thermal compartment based on the skin temperature data and to provide an indication of the core thermal compartment temperature on the display, wherein the temperature data is a skin temperature-versus-time dissipation curve, and wherein determination of the core thermal compartment temperature is established based on a slow temperature decrease portion of the temperature-versus-time curve determined by waiting for an empirically determined amount of time following the discontinuation of the heating, wherein the slow temperature decrease portion reflects a decreasing rate of change in the temperature measured by the skin temperature sensor and is indicative of reaching thermal equilibrium between the skin and the core thermal compartment.

42. The system of claim 41, wherein the indication of the core thermal compartment temperature corresponds to an intersection point of a first slope and a second slope, wherein the first slope is a rapid temperature decrease portion of the skin temperature-versus-time dissipation curve, and the second slope is the slow temperature decrease portion of the skin temperature-versus-time dissipation curve.

43. The system of claim 41, wherein the indication of the core thermal compartment temperature on the display is a graphical depiction of the skin temperature-versus-time dissipation curve.

44. The core temperature sensor of claim 1, wherein the core temperature is determined in less than 3 minutes.

* * * * *